(12) United States Patent
El Halawani et al.

(10) Patent No.: US 7,488,480 B2
(45) Date of Patent: Feb. 10, 2009

(54) USE OF PASSIVE MYOSTATIN IMMUNIZATION IN EGG LAYING VERTEBRATES

(75) Inventors: Mohamed E. El Halawani, St. Paul, MN (US); Seungkwon You, Suwon (KR)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 11/247,691

(22) Filed: Oct. 11, 2005
(Under 37 CFR 1.47)

(65) Prior Publication Data

US 2006/0088543 A1    Apr. 27, 2006

Related U.S. Application Data

(62) Division of application No. 09/754,826, filed on Jan. 4, 2001, now Pat. No. 7,037,501.

(51) Int. Cl.
*A61K 39/00* (2006.01)
*A61K 39/38* (2006.01)
*A61K 39/385* (2006.01)

(52) U.S. Cl. .................... 424/185.1; 424/193.1
(58) Field of Classification Search .............. None
See application file for complete search history.

(56) References Cited

U.S. PATENT DOCUMENTS

| | | | |
|---|---|---|---|
| 5,128,127 A | 7/1992 | Beck | |
| 5,827,733 A | 10/1998 | Lee et al. | |
| 5,994,618 A | 11/1999 | Lee et al. | |
| 6,096,506 A | 8/2000 | Lee et al. | |
| 6,369,201 B1 | 4/2002 | Barker et al. | |
| 7,037,501 B2 | 5/2006 | El Halawani et al. | |
| 7,070,784 B1 * | 7/2006 | Halkier et al. | 424/185.1 |

FOREIGN PATENT DOCUMENTS

| | | |
|---|---|---|
| GB | 2333706 | 8/1999 |
| WO | WO-98/33887 | 8/1998 |
| WO | WO-99/02667 | 1/1999 |
| WO | WO-99/06559 | 2/1999 |
| WO | WO-99/41081 | 8/1999 |
| WO | WO-99/42573 | 8/1999 |
| WO | WO-00/43781 | 7/2000 |
| WO | WO-01/05820 | 1/2001 |

OTHER PUBLICATIONS

Rock, Immunology Today, 1996, vol. 17 pp. 131-137.*
Dickman, S., "Gene Mutation Provides More Mear on the Hoof", *Science*, 277, (1997),pp. 1922-1923.
Goddard, I., et al., "TGB-beta (Transforming Growth Factor Beta) and its Related Peptides in the Testis", *Contraception, Fertilite, Sexualite*, 22 (9), (English Abstract Included in Article.),(Sep. 1994),pp. 564-570.
Grobet, L., et al., "A deletion in the bovine myostatin gene causes the double-muscled phenotype in cattle", *Nature Genetics*, 17 (1), (Sep. 1997),pp. 71-74.
Harris, J.R., et al., "Keyhole limpet hemocyanin (KLH): a biomedical review", *Micron 30*, (1999),pp. 597-623.
Ji, S., et al., "Myostatin expression in porcine tissues: tissue specificity and developmental and postnatal regualtion", *American Journal of Physiology*, 275 (4), (1998),pp. R1265-R1273.
Josso, N., et al., "TGF-beta Family Members and Gonadal Development", *Trends in Endocrinology*, 10 (6), (1999),pp. 216-222.
Josso, N., et al., "The role of anti-Mullerian hormone in gonadal development", *Molecular and Cellular Endocrinology*, 144 (1-2), (1998),pp. 3-7.
Kambadur, R., et al., "Mutations in myostatin (GDF8) in Double-Muscled Belgian and Piedmontese Cattle", *Genome Research*, 7 (9), (1997),pp. 910-916.
McPherron, A. C., et al., "Double muscling in cattle due to mutations on the myostatin gene", *Proc. Natl. Acad. Sci. U.S.A.*, 94 (23), (Nov. 11, 1997),pp. 12457-12461.
McPherron, A. C., et al., "Regulation of skeletal muscle mass in mice by a new TGF-beta superfamily member", *Nature*, 387, (May 1997),pp. 83-90.
Ngo, J T., "Computational Complexity, Protein Structure Prediction, and the Levinthal Paradox", In: *The Protein Folding Problem and Tertiary Structure Prediction*, Merz, Jr., K., et al., (eds.), Birkhauser, Boston,(1994),491-495.
Skolnick, J., "From Genes to Protein Structure and Function: Novel Applications of Computational Approaches in the Genomic Era", *TIBTECH*, 18, (Jan. 2000),34-39.
Van Der Kruijssen, C. M., et al., "Modulation of Activin Expression by Type beta Transforming Growth Factors", *Experimental Cell Research*, 207 (2), (1993),pp. 407-412.
Westhusin, M., "From mighty mice to mighty cows", *Nature Genetics*, 17 (1), (Sep. 1997),pp. 4-5.

* cited by examiner

*Primary Examiner*—Michail A Belyavskyi
(74) *Attorney, Agent, or Firm*—Schwegman, Lundberg & Woessner

(57) ABSTRACT

A method to alter the phenotype of animals, e.g., the progeny of egg laying vertebrates, which employs passive immunization, is provided.

8 Claims, 20 Drawing Sheets

GDF-8

DNA SEQUENCE

GATTTTGGCCTTGACTGCGACGAGCACTCAACGGAATCTCGATGTTGTCGCTA
CCCGCTGACAGTGGATTTTGAAGCTTTTGGATGGGACTGGATTATAGCACCTA
AAAGATACAAAGCCAATTACTGCTCTGGAGAATGTGAATTCGTATTTCTACA
GAAATACCCGCACACTCACCTGGTACACCAAGCAAATCCAAGAGGCTCAGCA
GGCCCTTGCTGCACACCCACCAAGATGTCCCCTATAAACATGCTGTATTTCAA
TGGAAAAGAACAAATAATATATGGAAAGATACCAGCCATGGTTGTAGATCGT
TGCGGGTGCTCATGAGAC

SEQ ID NO:1

PROTEIN SEQUENCE

DFGLDCDEHSTESRCCRYPLTVDFEAFGWDWIIAPKRYKANYCSGECEFVFLQK
YPHTHLVHQANPRGSAGPCCTPTLMSPINMLYFNGKEQIIYGKIPAMVVDRCGCS

SEQ ID NO:2

FIG. 1

Whole Live Turkeys
( Immunized vs Control)

Breast Muscle
( Immunized vs Control)

Breast
( Immunized vs Control)

Thigh Muscle
( Immunized vs Control)

Abdominal Fat
( Immunized vs Control)

Testis
( Immunized vs Control)

Heart

( Immunized vs Control)

USE OF PASSIVE MYOSTATIN IMMUNIZATION IN EGG LAYING VERTEBRATES

RELATED APPLICATIONS

This application is a divisional of U.S. patent application Ser. No. 09/754,826, filed Jan. 4, 2001, now U.S. Pat. No. 7,037,501, issued May 2, 2006, which is incorporated herein by reference.

BACKGROUND OF THE INVENTION

The transforming growth factor β (TGF-β) superfamily encompasses a group of structurally related proteins. The proteins of the TGF-β family are initially synthesized as a large precursor protein which subsequently undergoes proteolytic cleavage at a cluster of basic residues approximately 110-140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. The active species appears to be a disulfide-linked dimer of C-terminal fragments (Hammonds et al., 1991), although for some family members (Ling et al., 1986; Cheifetz et al., 1987), heterodimers have also been detected and appear to have different biological properties than the respective homodimers.

The TGF-β family includes Mullerian inhibiting substance (MIS) (Behringer et al., 1990), which is required for normal male sex development, Drosophila decapentaplegic (DPP) gene product, which is required for dorsal-ventral axis formation and morphogenesis of the imaginal disks (Padgett et al., 1987), the Xenopus Vg-1 gene product, which localizes to the vegetal pole of eggs (Weeks et al., 1987), the activins, which can induce the formation of mesoderm and anterior structures in Xenopus embryos (Thomsen et al., 1991), and the bone morphogenetic proteins (BMPs, osteogenin, OP-1) which can induce de novo cartilage and bone formation (Sampath et al., 1990). Another member of the TGF-β superfamily, myostatin (also known as growth/differentiation factor-8 or GDF-8), is synthesized by skeletal muscle, and regulates the proliferation and differentiation of myoblasts. The members of the TGF-β family can thus influence a variety of differentiation processes, including adipogenesis, myogenesis, chondrogenesis, hematopoesis, and epithelial cell differentiation (Massague, 1987).

Because the members of the TGF-β family are involved in differentiation, the association of a particular TGF-β member with a certain characteristic in an animal and the manipulation of the expression of the gene(s) associated with that characteristic is of interest. For example, muscle mass in Belgian Blue cattle, due primarily to hyperplasia of muscle cells, is increased by approximately 20% (referred to as double-muscling) with a corresponding decrease in bone and fat mass (Shahin and Berg, 1985). Belgian Blue cattle are particularly valuable livestock as they utilize feed efficiently and give rise to a higher percentage of desirable cuts of meat (Casas et al., 1997). Double-muscling in Belgian Blue cattle was observed to be an inherited trait that was recessive because heterozygotes were normal or had only a modest increase in muscle mass. Molecular analyses found that these cattle expressed a non-functional myostatin protein (see, e.g., WO 99/02667). Another breed of cattle, the Piedmontese, and myostatin gene knock-out mice, also exhibit double-muscling (McPherron and Lee, 1997; Grobet et al., 1997; McPherron et al., 1997; Kambadur et al., 1997). Thus, myostatin has been hypothesized to regulate the amount of skeletal muscle mass in a negative manner.

To prepare transgenic species having increased muscle tissue, e.g., for livestock with high muscle and protein content, the delivery of mutated myostatin genes to animals has been proposed. See, e.g., WO 98/33887. Despite the advantages of double-muscling, double-muscled cattle often have undesirable traits. The myostatin gene becomes active during the embryonic stage, and any reduction in myostatin production causes excessive muscle development in utero, leading to larger offspring. Belgian Blue calves are generally 10-38% heavier than normal, dystocias are prevalent, requiring cesarean deliveries. These animals also exhibit abnormal reproduction due to poorly developed reproductive tracts and have other anatomical abnormalities such as macroglossia. Thus, transgenic animals having mutated myostatin genes, like Belgian Blue cattle, would likely require cesarean delivery and exhibit anatomical abnormalities, a serious burden to large animal producers. Additionally, there is public opposition to genetically engineered animals for human consumption.

Thus, what is needed is a method to prepare non-transgenic animals having increased muscle mass, preferably without an increase in fat content, as well as having acceptable performance, e.g., the animals utilize feed efficiency, and retain reproductive function and general health.

SUMMARY OF THE INVENTION

The present invention is directed to immunological compositions and methods for modulating endogenous GDF, e.g., GDF-8 (myostatin), activity in a vertebrate and its progeny, e.g., a vertebrate including but not limited to, an avian, e.g., turkey, chicken, ostrich, game birds and water fowl, a mammal, e.g., bovine, equine, porcine, caprine, and ovine and aquatic animals such as crustaceans, e.g., shrimp and lobster, and fish. Preferably, the vertebrate is a livestock animal, i.e., animals used for human consumption. The invention is directed to both passive and active immunization of non-human vertebrates, including in ovo immunization. Although immunization against endogenous molecules, such as myostatin, is problematic because the immune system does not recognize "self" molecules, surprisingly, as described hereinbelow, the progeny of myostatin-immunized female vertebrates had at least one desired characteristic associated with an alteration in the level or activity of at least one member of the TGF-beta superfamily, e.g., GDFs (for example, any one of GDF 1-11), inhibins (for example, inhibin-alpha, inhibin-beta-alpha, and inhibin beta-beta), activins, follistatin, macrophage inhibition cytokine (MIC-1), bone morphogenic proteins (BMPs, for example any one of BMP 1-5 or OP-1), Vgr-1, CP-1, MIS, TGF-beta (for example, any one of TGF-beta1, TGF-beta2 or TGF-beta-3) and glial derived neurotrophic factor. Thus, the invention provides a vaccine or immunogenic composition useful to elicit an immune response to one or more polypeptides in the TGF-beta superfamily, e.g., GDF polypeptides including, but not limited to GDF-7, GDF-8, GDF-9 or GDF-11, in a vertebrate so as to result in the vertebrate or its progeny having at least one desired characteristic as a result of the immune response.

In one embodiment, the vaccine or immunogenic composition may be a fusion protein which comprises at least a portion of a GDF, e.g., myostatin, polypeptide, an immunoconjugate which comprises at least a portion of a GDF polypeptide or a polynucleotide which encodes at least a portion of a GDF polypeptide, e.g., in the form of a recombinant vector. In particular, the use of a vaccine comprising a full length, e.g., the mature form, GDF polypeptide which has a large number of epitopes (relative to a peptide immunogen), some of which may be common to other members of the TGF-beta superfamily, is preferred. A peptide may be employed as an immunogen to obtain the desired result(s), however, the administration of peptide immunogens are less likely to result in effective increases in IgG, e.g., in the embryo, and as strong an immune response as that which results from the administration of a larger, e.g., full length polypeptide, immunogen.

In one embodiment of the invention, the method comprises the administration of a myostatin immunogen, such as a full length (mature form of) myostatin, to a female vertebrate prior to, during, and/or after fertilization of an egg(s) in an amount which results in the alteration of the level and/or activity of at least one member of the TGF-beta superfamily yielding progeny having at least one desirable characteristic. For example, the alteration may be a decrease in the level and/or activity of myostatin in the immunized vertebrate and its progeny. Desirable characteristics include but are not limited to an increase in muscle mass, an increase in body weight, a decrease in body fat, an increase in testes size, an increase in muscle mass, an increase in the number of muscle cells, an increase in the size of muscle cells, a reduction in body fat content, an increase in muscle strength, an increase in appetite or feed uptake, an increase in the life span, or any combination thereof.

As described herein, the active immunization of a turkey hen against myostatin resulted in the passive immunization of the offspring (turkey poults) against myostatin, i.e., anti-myostatin antibodies were transferred from hens to poults through eggs. The immunized poults were larger than control poults and had an increase in breast muscle, thigh muscle, testes and heart weight, and no significant change in breast bone, gut or liver weight relative to control poults. Surprisingly, abdominal fat weight was decreased by 50% in immunized poults relative to controls. Maternal myostatin antibodies likely neutralized endogenous myostatin during embryonic development and removed the inhibitory effect of myostatin on skeletal muscle development and growth, thus stimulating the growth rate of the hatched poults.

In one embodiment of the invention, progeny of immunized females have an increase in body weight, e.g., an increase of at least 1% to 10%, preferably at least 15%, more preferably at least 20%, and even more preferably at least 50% or more relative to control animals, enhanced muscle mass, e.g., in avians an increase of at least 1% to 10%, preferably at least 5% to 20%, more preferably at least 30%, and even more preferably at least 33% or more in skeletal muscle mass, relative to control animals, increased muscle strength, an alteration in the ratio of muscle to fat, an increase in fat-free muscle mass, an increase in the size and/or number of muscle cells, a reduction in body fat content, e.g., a decrease of at least 1% to 5%, more preferably at least 10%, and even more preferably at least 20% or more in fat, e.g., abdominal fat, relative to control animals, an increase in testis weight in males, e.g., at least 10%, preferably at least 50%, more preferably at least 100% up to 200%, and even more preferably at least 300%, greater than control animals, and an increase in appetite or feed uptake. Moreover, unlike progeny of genetically engineered vertebrates, such as myostatin "knock out" vertebrates, the effect of the immunization of the female on her progeny is not heritable.

The compositions and methods of the present invention reduce GDF, e.g., myostatin, activity or levels in the immunized female vertebrate animal as well as progeny thereof. A reduction in the activity or level of at least one GDF may be a result of the reduction of circulating levels of GDFs normally found in a vertebrate or its progeny due to inactivation of circulating GDFs by anti-GDF antibodies. For example, the reduction may be a result of the reduction of circulating levels of myostatin normally found in a vertebrate or its progeny due to inactivation of circulating myostatin by anti-GDF antibodies including anti-myostatin antibodies. However, the reduction of GDF, e.g., myostatin, activity or levels may be the result of decreased production or secretion of GDF(s) into the circulation. Moreover, the GDF immunogens may elicit the production of antibodies which prevent at least one of the GDFs such as myostatin from being cleaved to release the active portion of the protein, or prevent the protein from binding to its receptor. Alternatively, the antibodies may remove at least one secreted GDF, for example, secreted myostatin, from the circulation or other body fluids. The characteristic(s) in the progeny are the result of the passive transmission of maternal antibodies against GDF, e.g., myostatin, to the progeny, e.g., in ovo or in utero. In ovo vaccination may be conducted as described in Kocamis et al. (1998). Hence, the active immunization of the female results in the passive immunization of progeny of the immunized female. The transmission of neutralizing maternal antibodies may occur transplacentally to the fetus, in the colostrum to the neonate of an immunized female, in ovo or by post-natal transfer of maternal antibodies by non-physiological routes, e.g., by injection. The invention also includes the administration of anti-TGF-beta superfamily polypeptide antibodies, such as monoclonal, polyclonal and/or anti-idiotype antibodies, fragments thereof, e.g., scFv, Fab, F(ab')$_2$, or Fv, or other modified forms thereof, e.g., chimeras including grafted CDRs, to another vertebrate.

The immunogens of the invention may be particularly useful in turkey and swine production. In the turkey industry, most progeny are produced by artificial insemination (the cost of semen per egg is about 5 cents and in the U.S. approximately 400 million eggs are inseminated per year) and it takes up to 30 weeks to bring a tom into production. In the swine industry, almost 90% of progeny are obtained by artificial insemination (at about $6/dose). Thus, a decrease in the time to production and/or an increase in the amount of semen obtained per male, is highly desirable. Thus, the method of the invention yields immunized male livestock or male progeny of immunized female livestock with increased testes size and preferably results in an increase in semen obtainable per male. In addition, immunized (passive or active) males reproductively mature sooner.

Thus, in one embodiment of the invention, the compositions and methods of the invention reduce the activity and/or level of at least one GDF in an immunized female vertebrate yielding male progeny having an increase in testes size or an immunized male vertebrate having an increased testis size. The increase in testis weight in males is preferably at least 10%, more preferably at least 50%, even more preferably at least 100% up to 200%, and yet even more preferably at least 300%, greater than control animals. Preferred vertebrates to be immunized are avians and swine.

BRIEF DESCRIPTION OF THE FIGURES

FIG. 1 depicts the nucleotide sequence (SEQ ID NO: 1) and inferred amino acid sequence (SEQ ID NO:2) of turkey myostatin (GDF-8).

DETAILED DESCRIPTION OF THE INVENTION

A. Definitions

Figure 2:
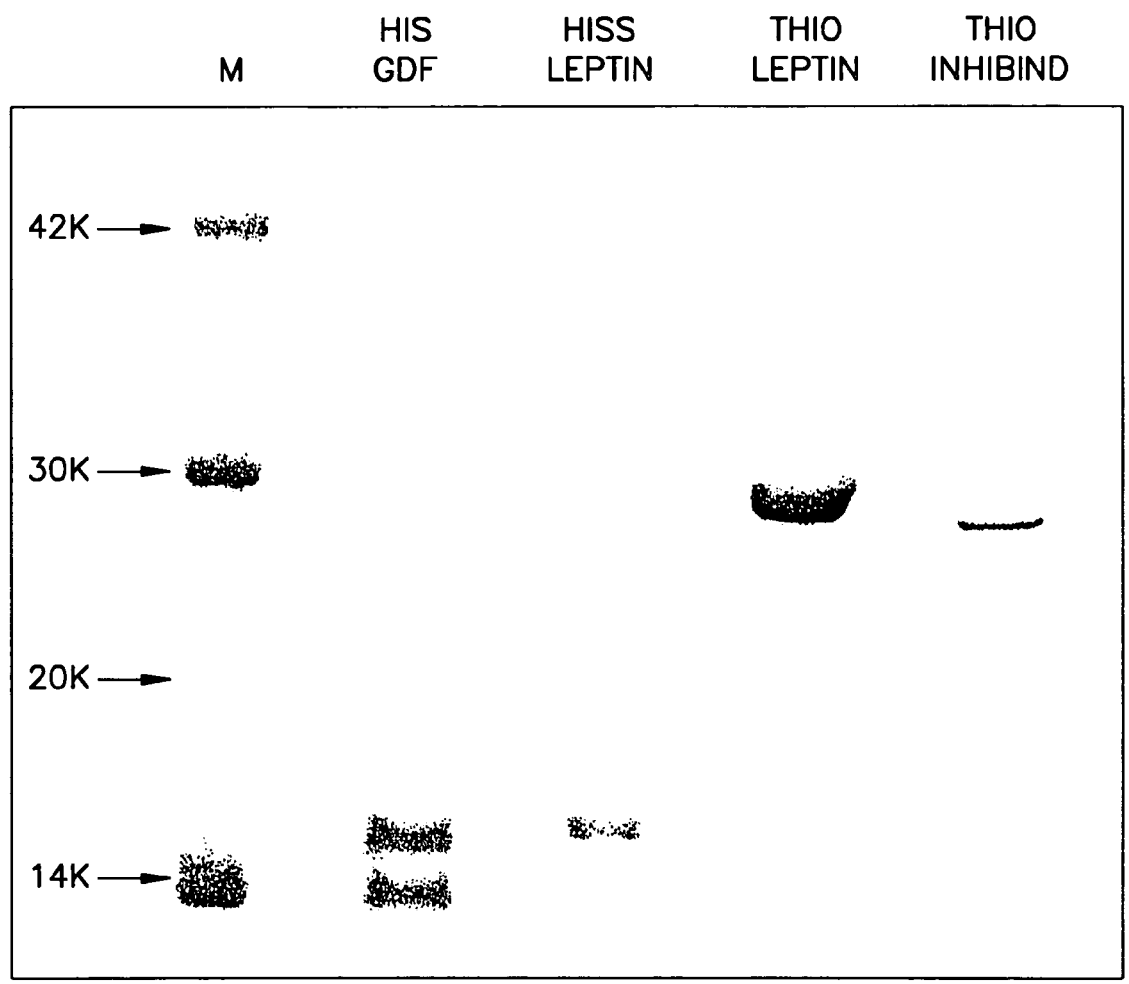
FIG. 2 is a SDS-PAGE gel with a His-tag GDF-8 fusion protein and the amino terminal sequence of such a fusion protein (SEQ ID NO:3).
Figure 3:
FIG. 3 shows the relative size of progeny from an immunized turkey versus a control turkey.
Figure 4:
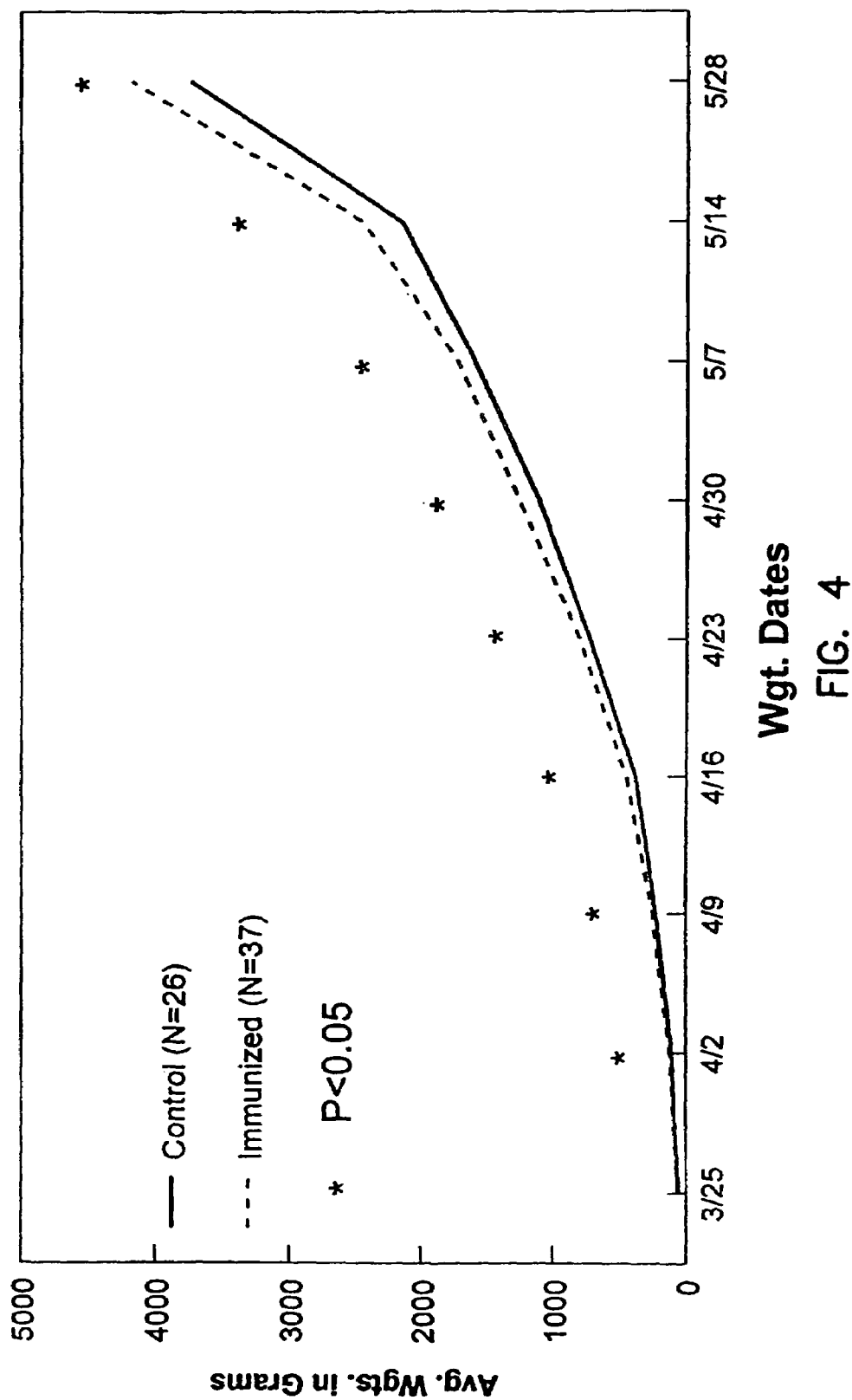
FIG. 4 is a graph depicting the growth curve for male progeny from immunized turkeys versus control turkeys.
Figure 5:
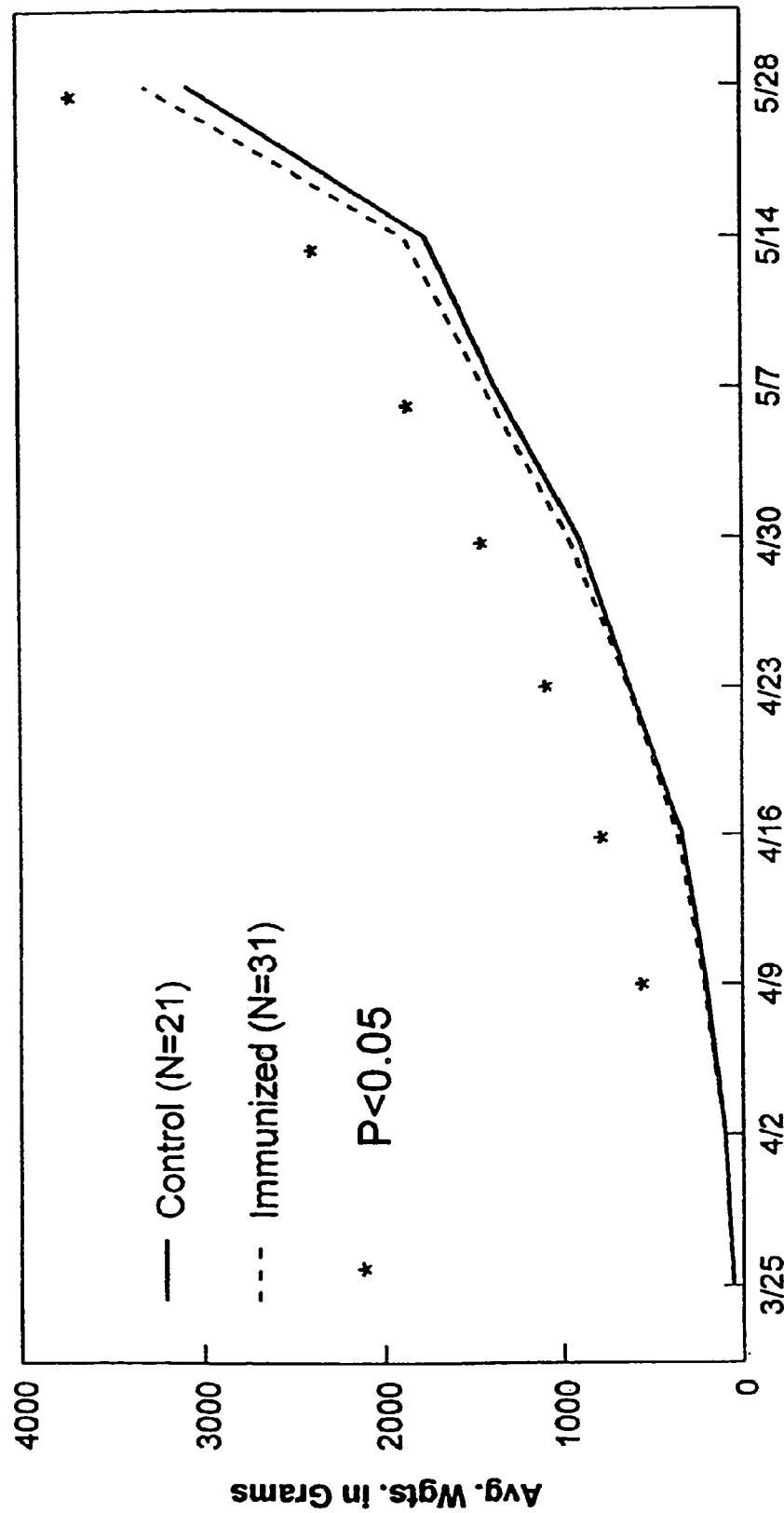
FIG. 5 is a graph depicting the growth curve for female progeny from immunized turkeys versus control turkeys.
Figure 6:
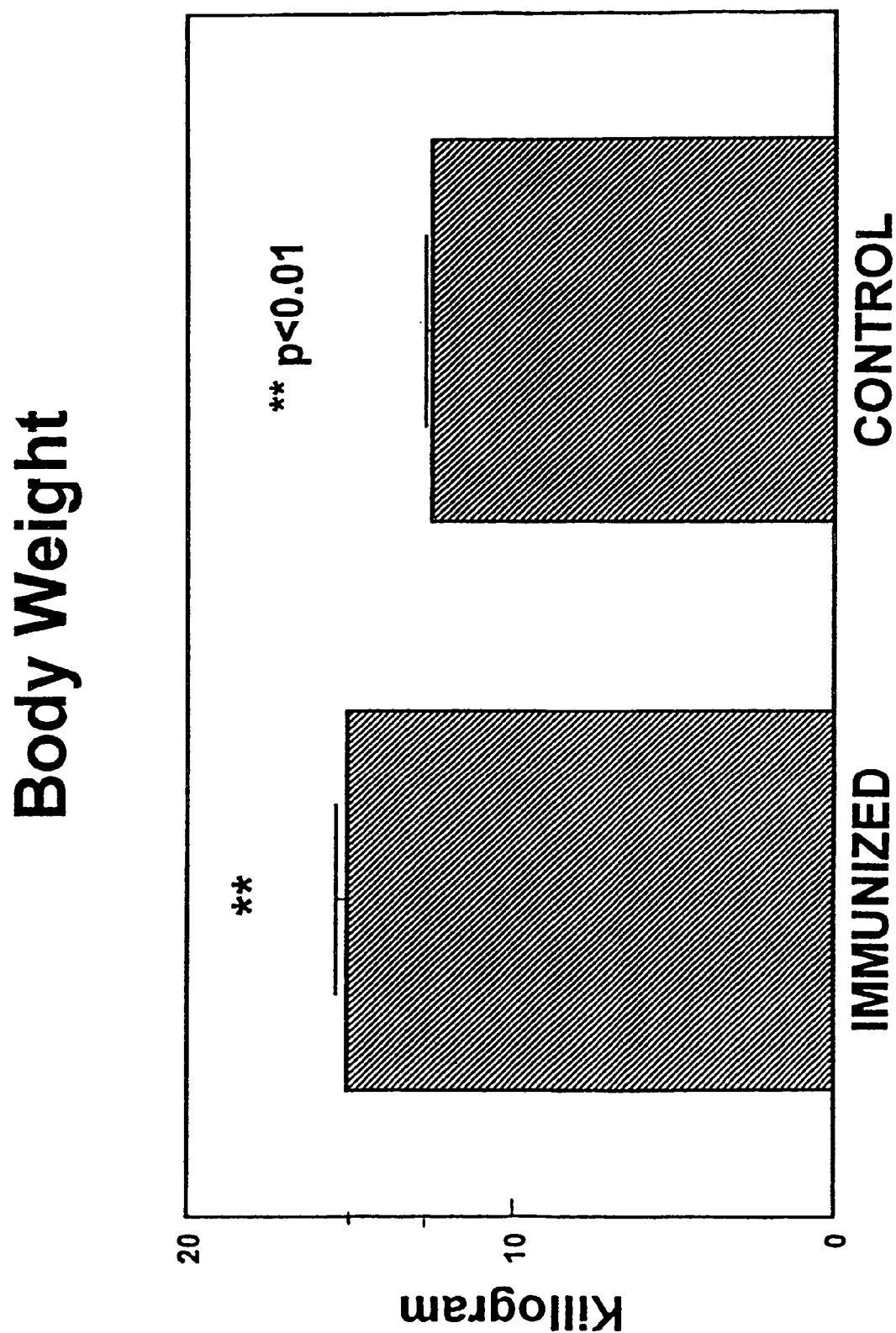
FIG. 6 shows the average body weight for progeny from immunized turkeys and control turkeys.
Figure 7:
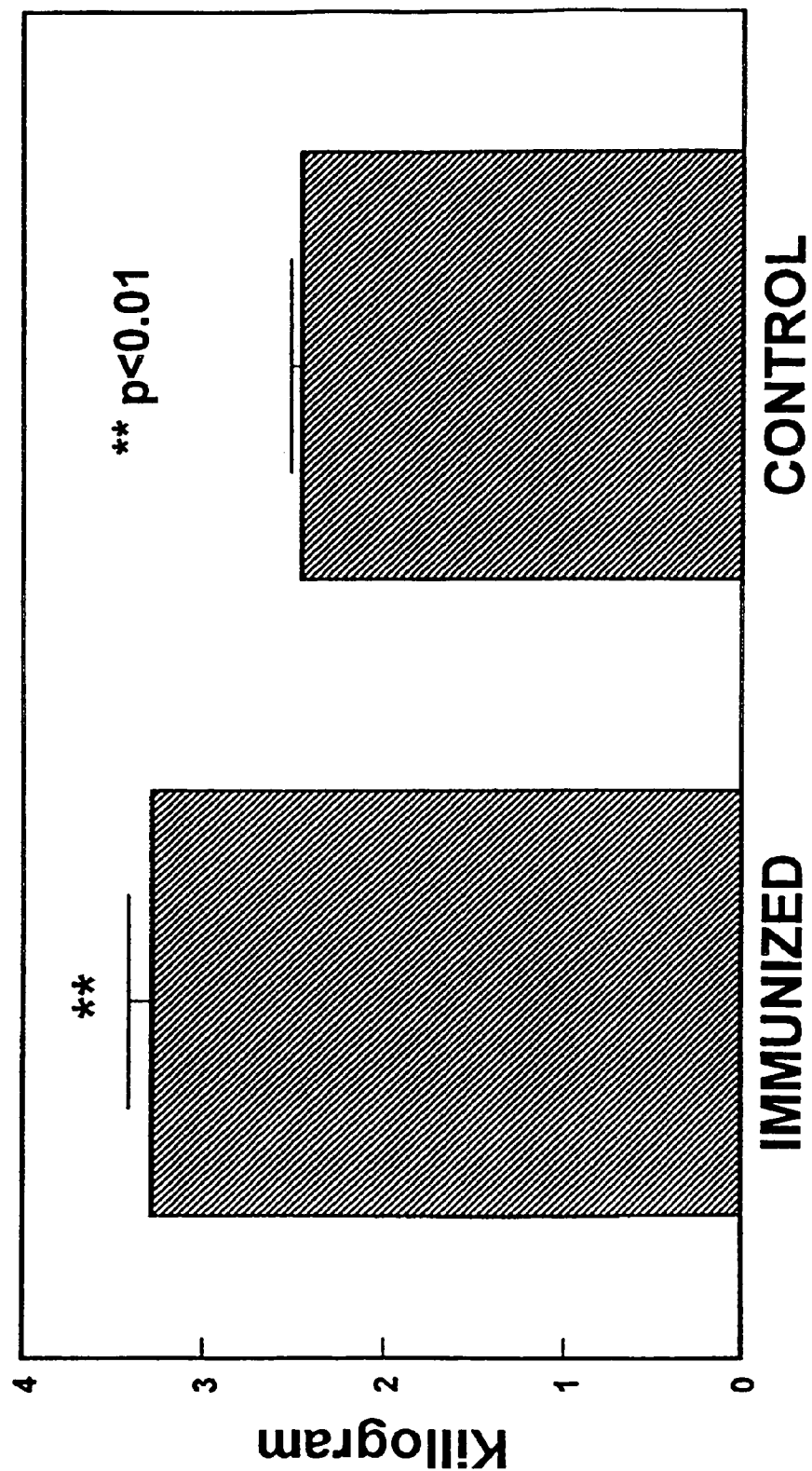
FIG. 7 shows the average breast muscle weight for progeny from immunized turkeys and control turkeys.
Figure 8:
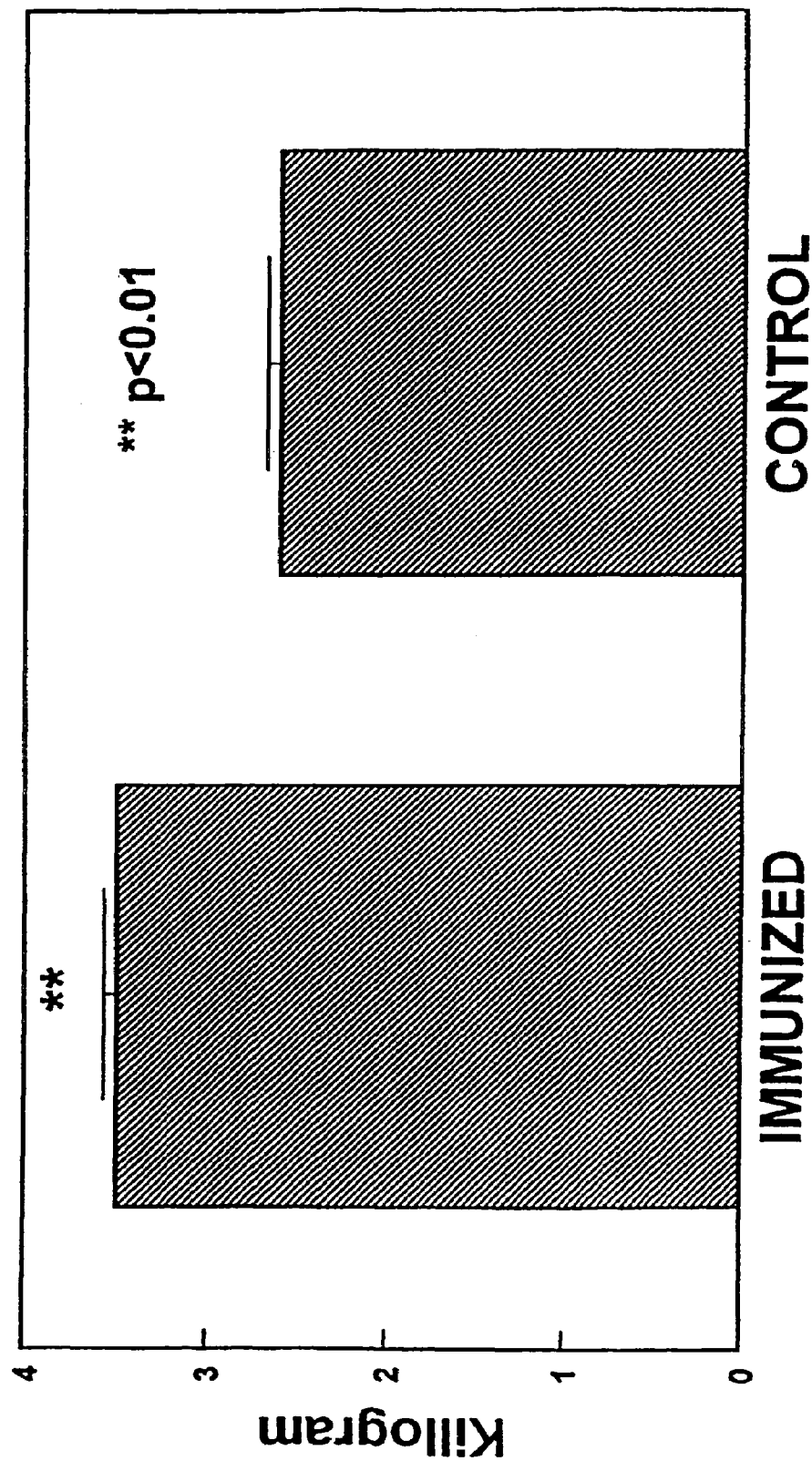
FIG. 8 shows the average thigh muscle weight for progeny from immunized turkeys and control turkeys.
Figure 9:
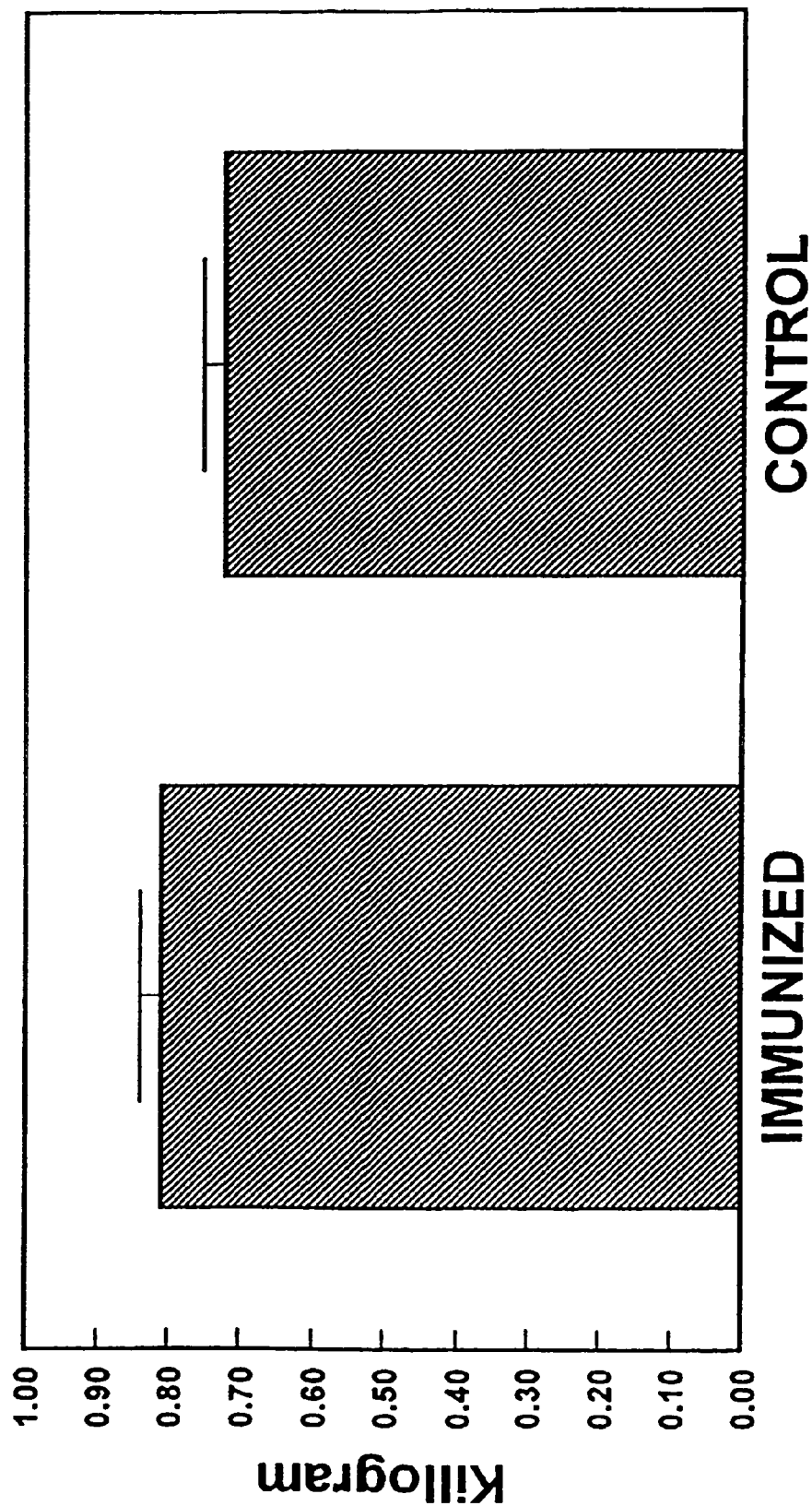
FIG. 9 shows the average breast bone weight for progeny from immunized turkeys and control turkeys.
Figure 10:
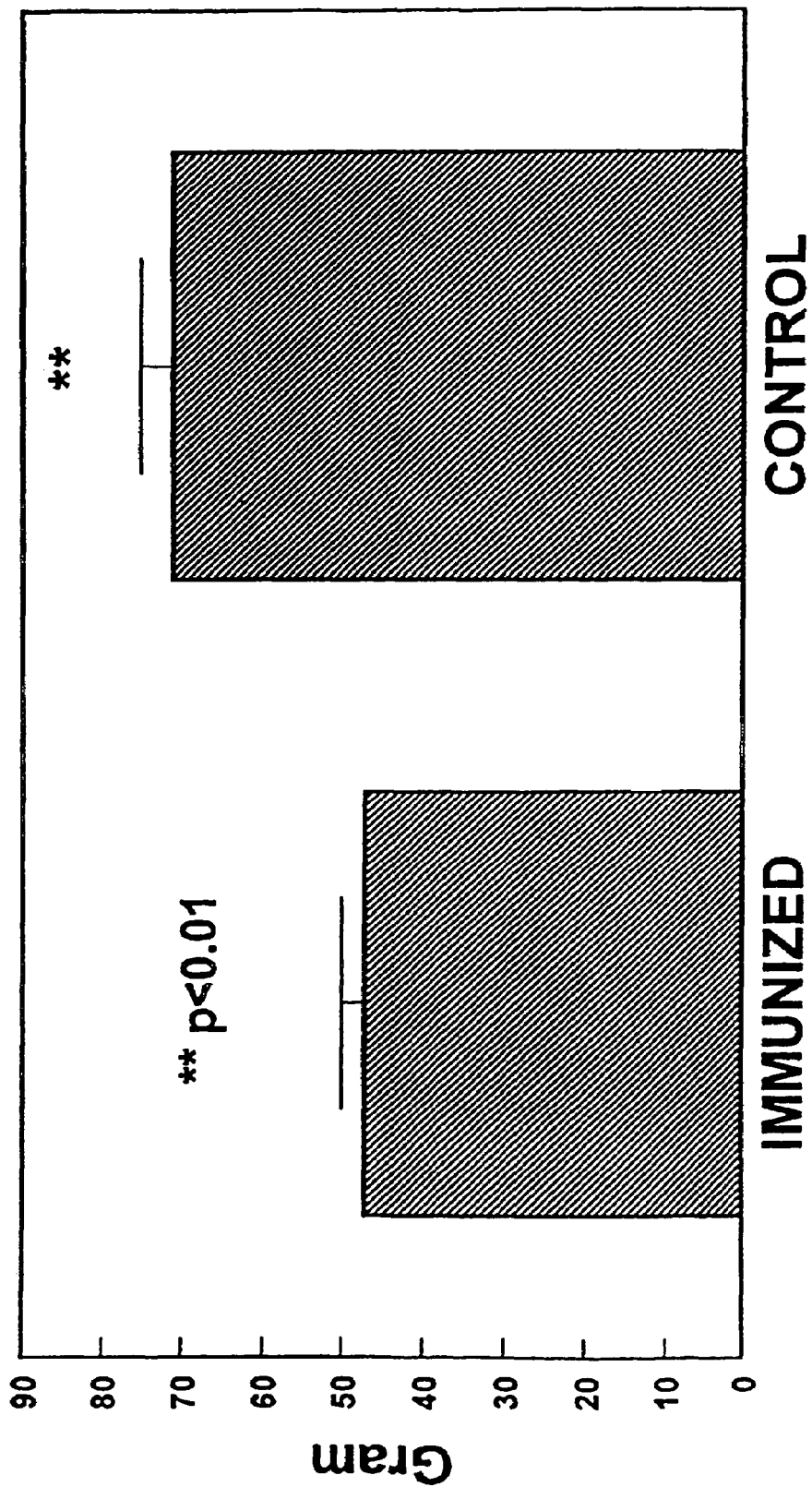
FIG. 10 depicts the average abdominal fat weight in progeny from immunized turkeys and control turkeys.
Figure 11:
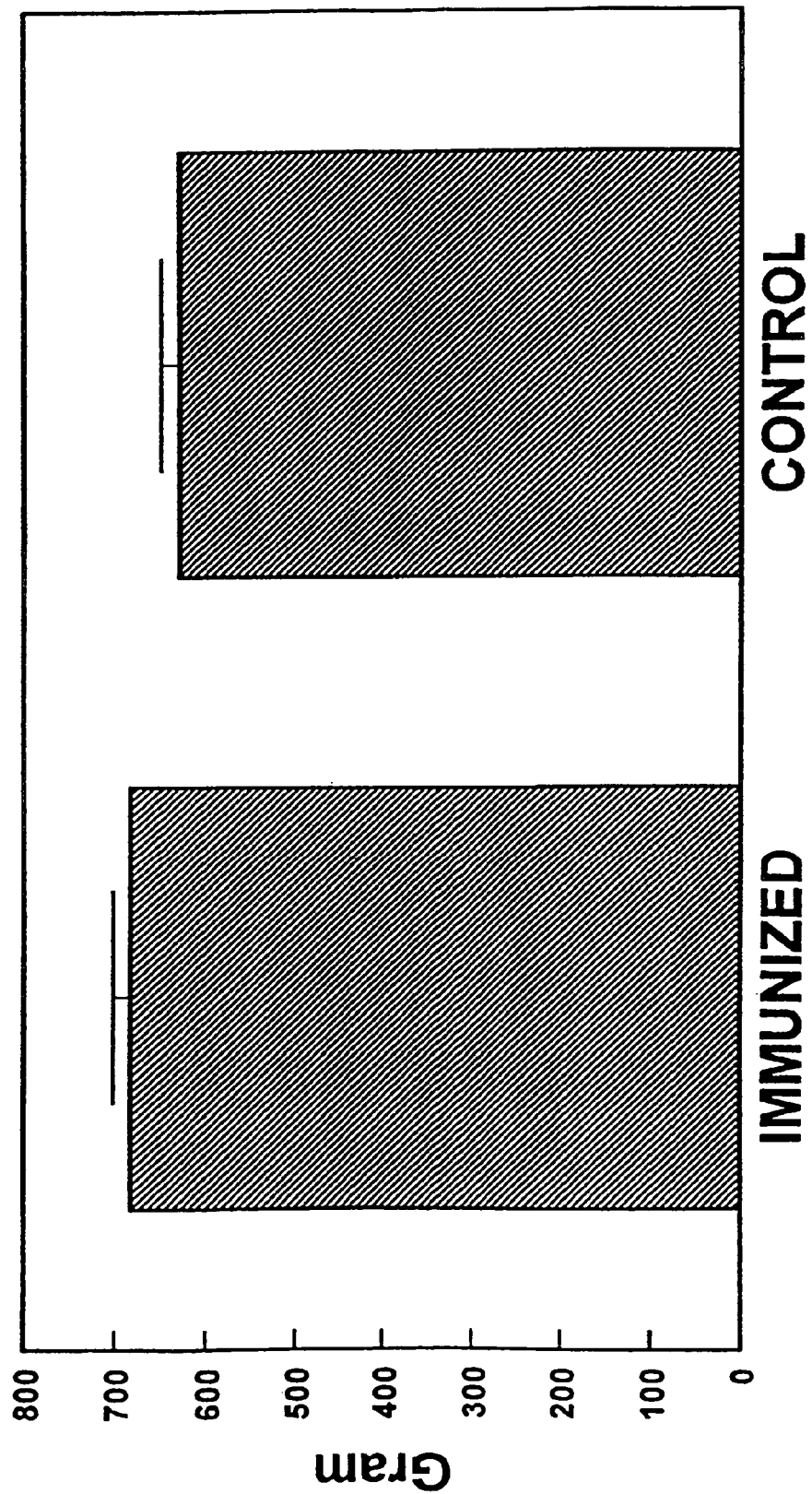
FIG. 11 depicts the average gut weight in progeny from immunized turkeys and control turkeys.
Figure 12:
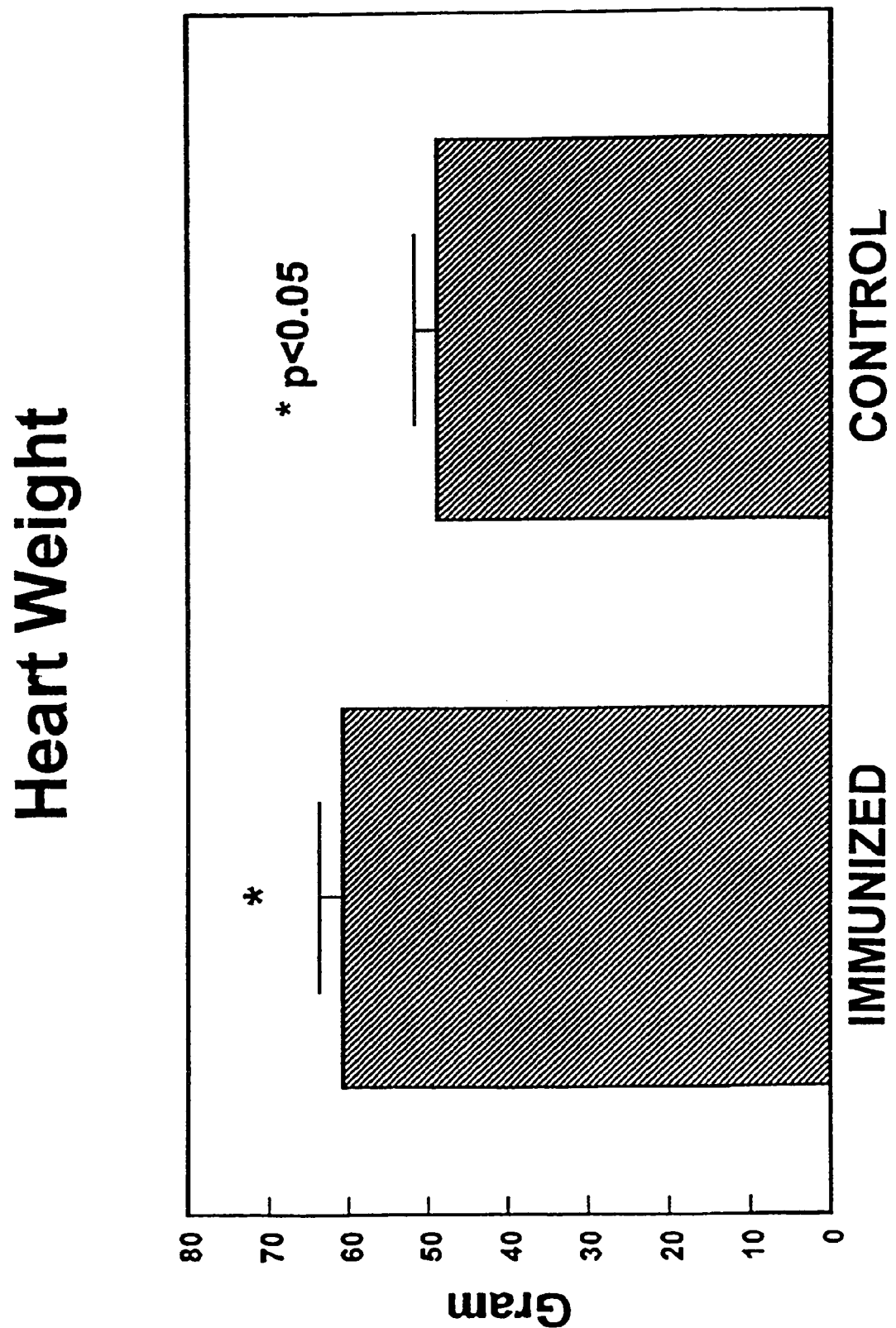
FIG. 12 depicts the average heart weight in progeny from immunized turkeys and control turkeys.
Figure 13:
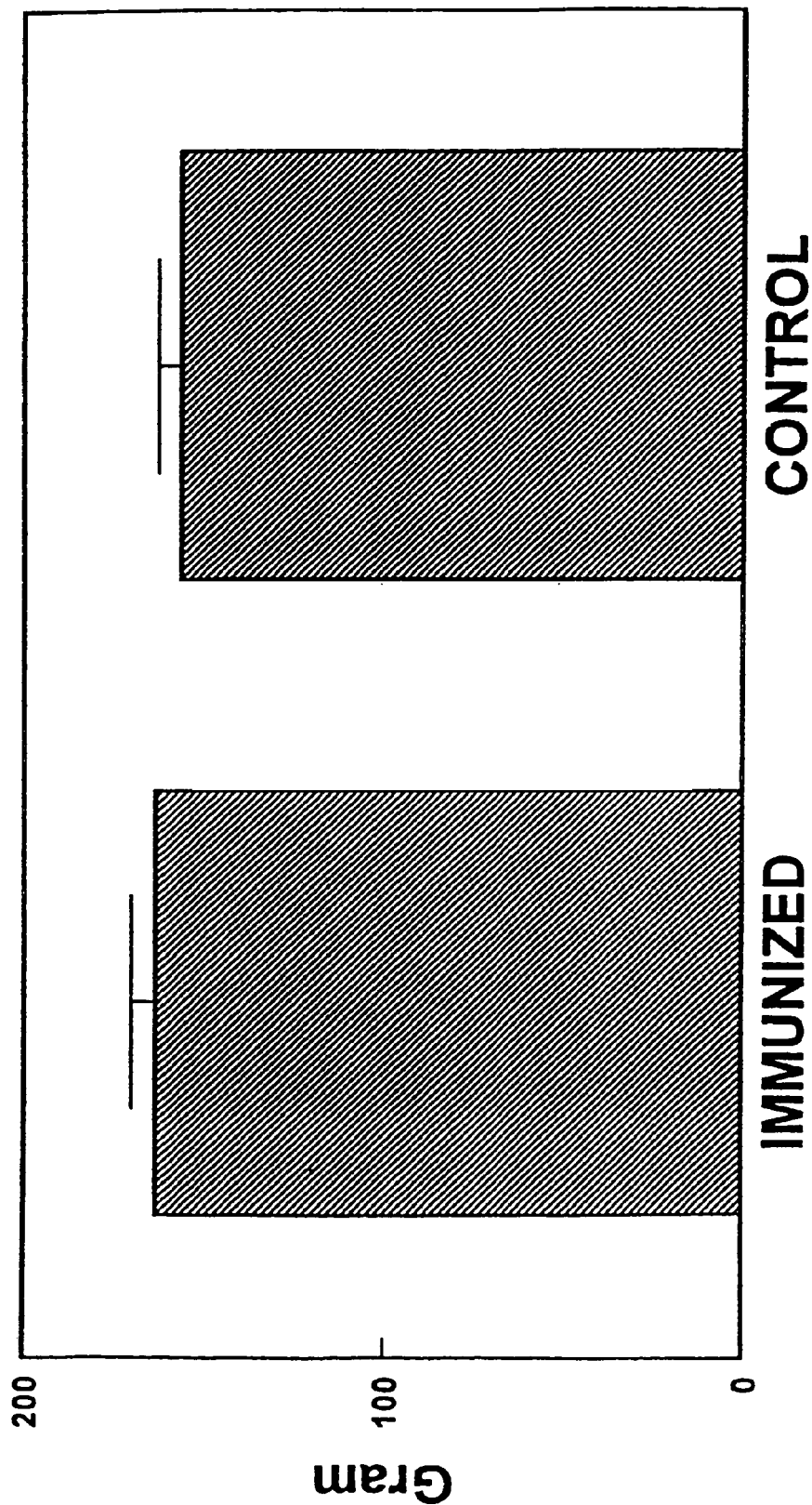
FIG. 13 depicts the average liver weight in progeny from immunized turkeys and control turkeys.
Figure 14:
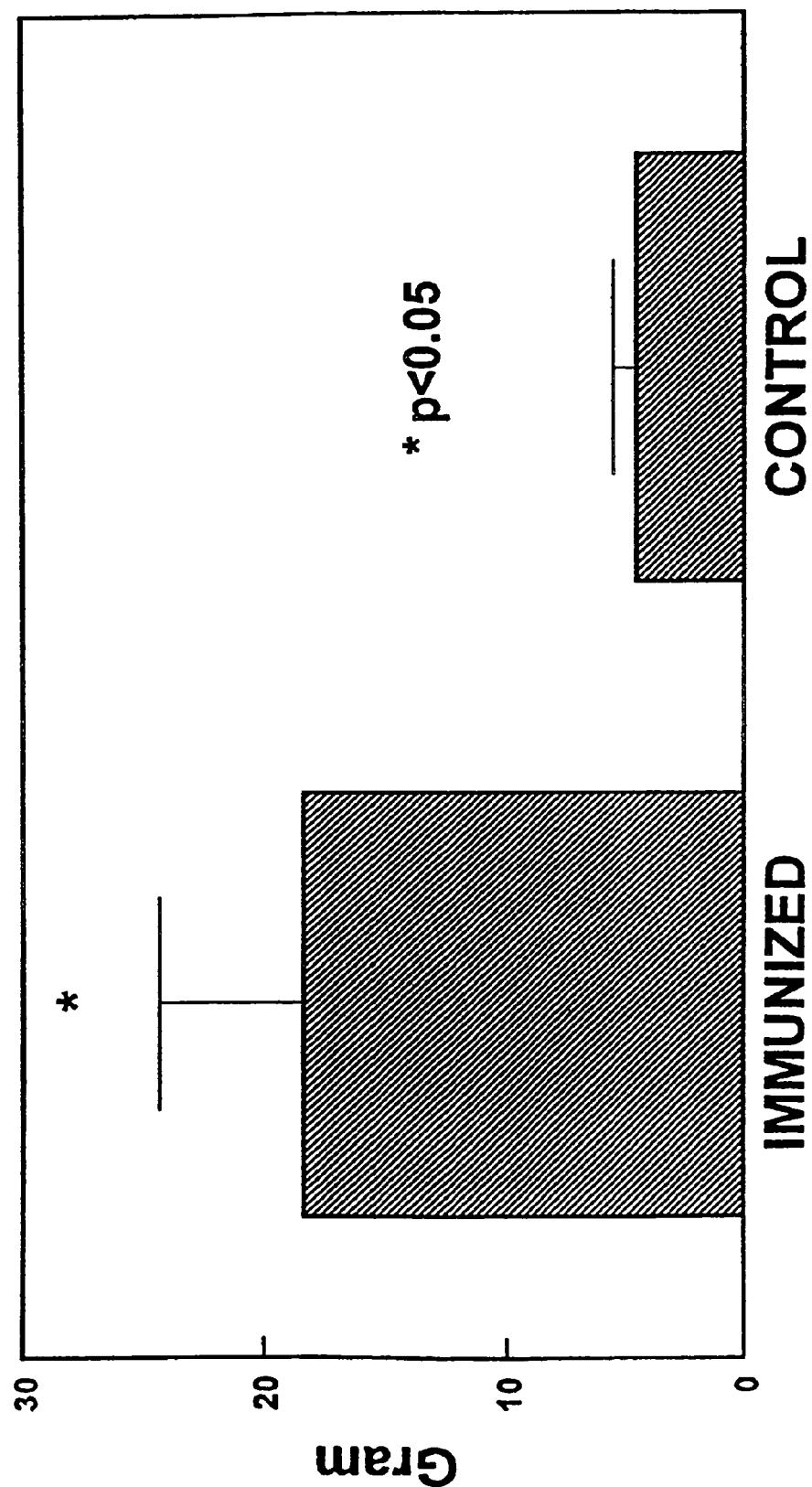
FIG. 14 depicts the average testis weight in progeny from immunized turkeys and control turkeys.
Figure 15:
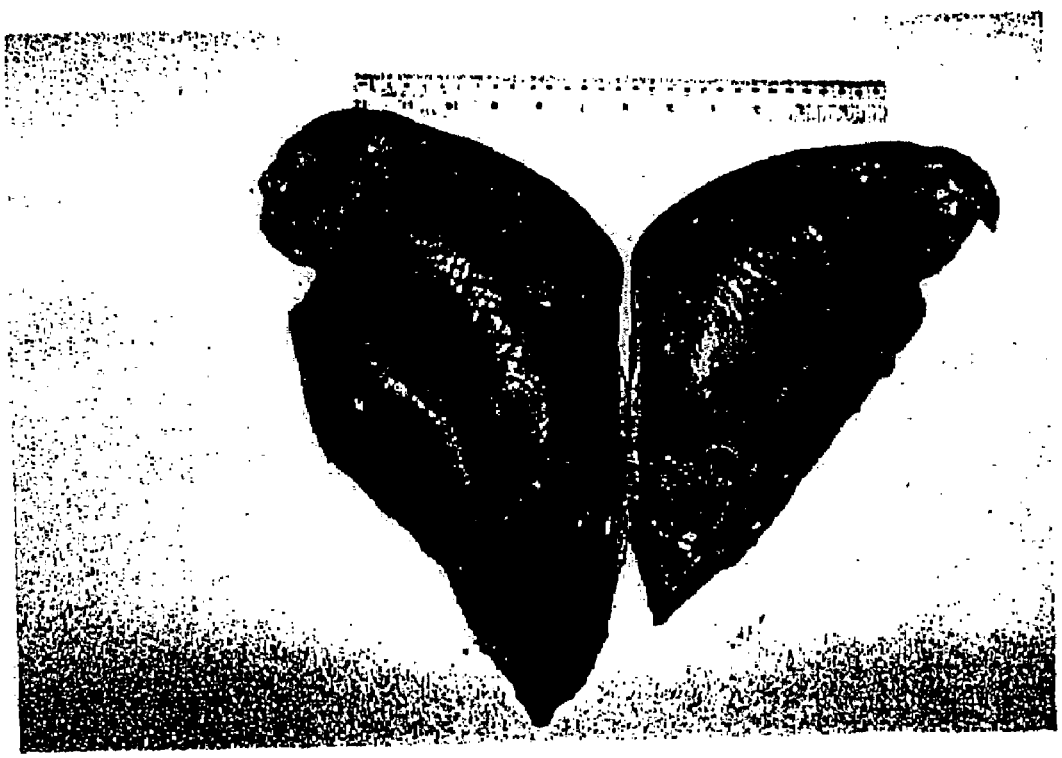
FIG. 15 shows an example of breast muscle from progeny of an immunized turkey and a control turkey.
Figure 16:
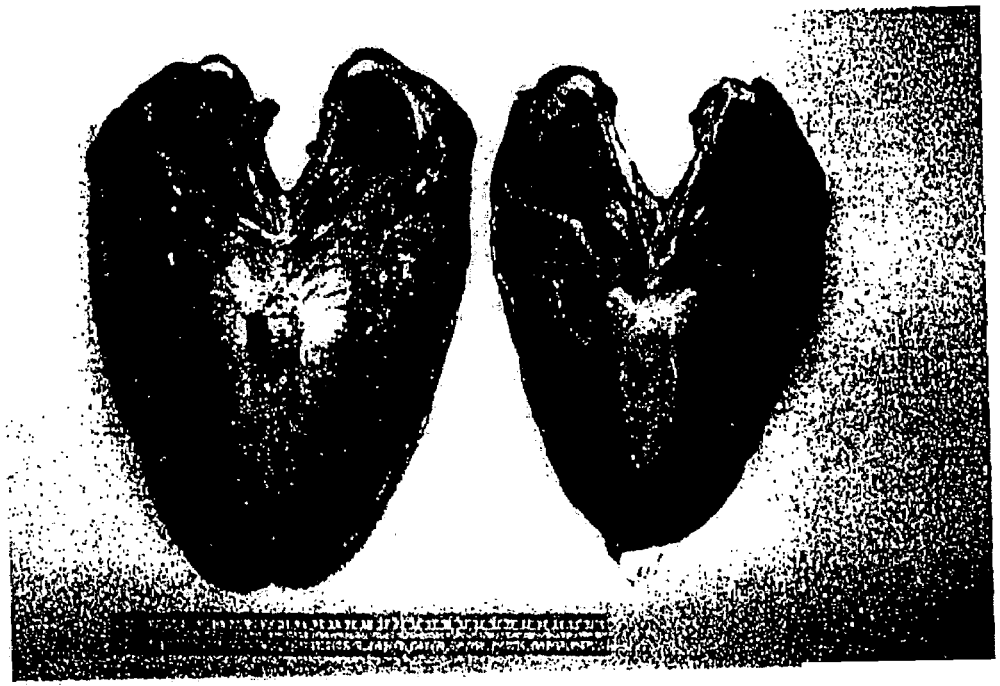
FIG. 16 shows an example of a breast from progeny of an immunized turkey and a control turkey.
Figure 17:
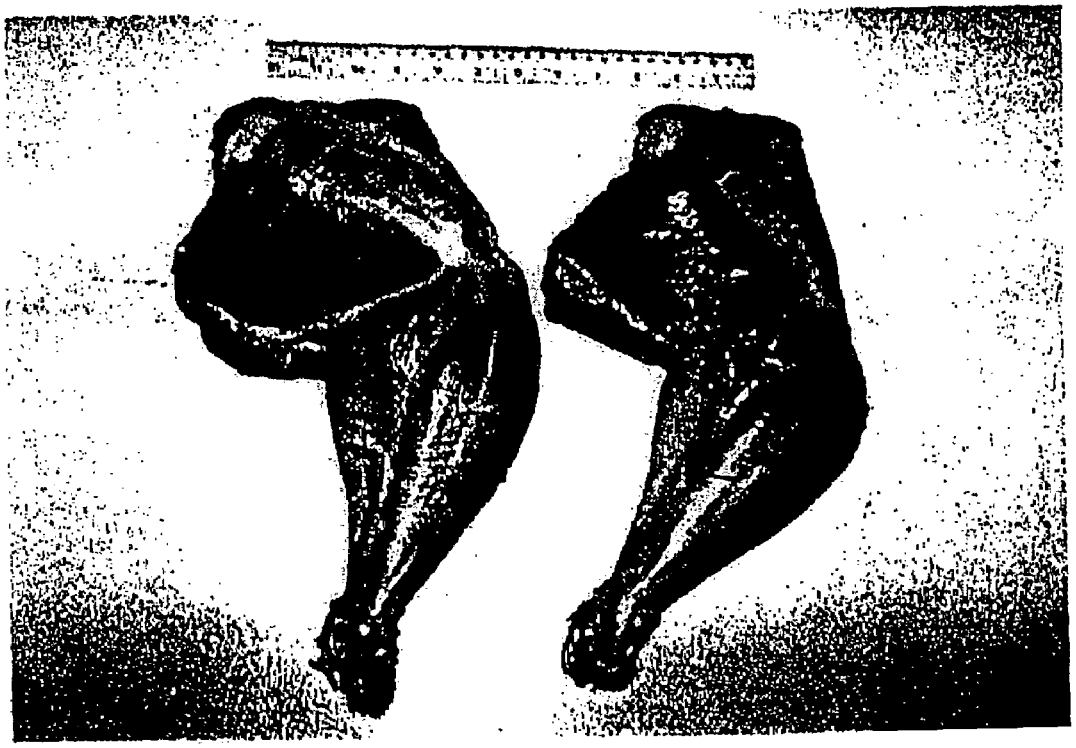
FIG. 17 shows an example of thigh muscle from progeny of an immunized turkey and a control turkey.
Figure 18:
FIG. 18 shows an example of abdominal fat from progeny of an immunized turkey and a control turkey.
Figure 19:
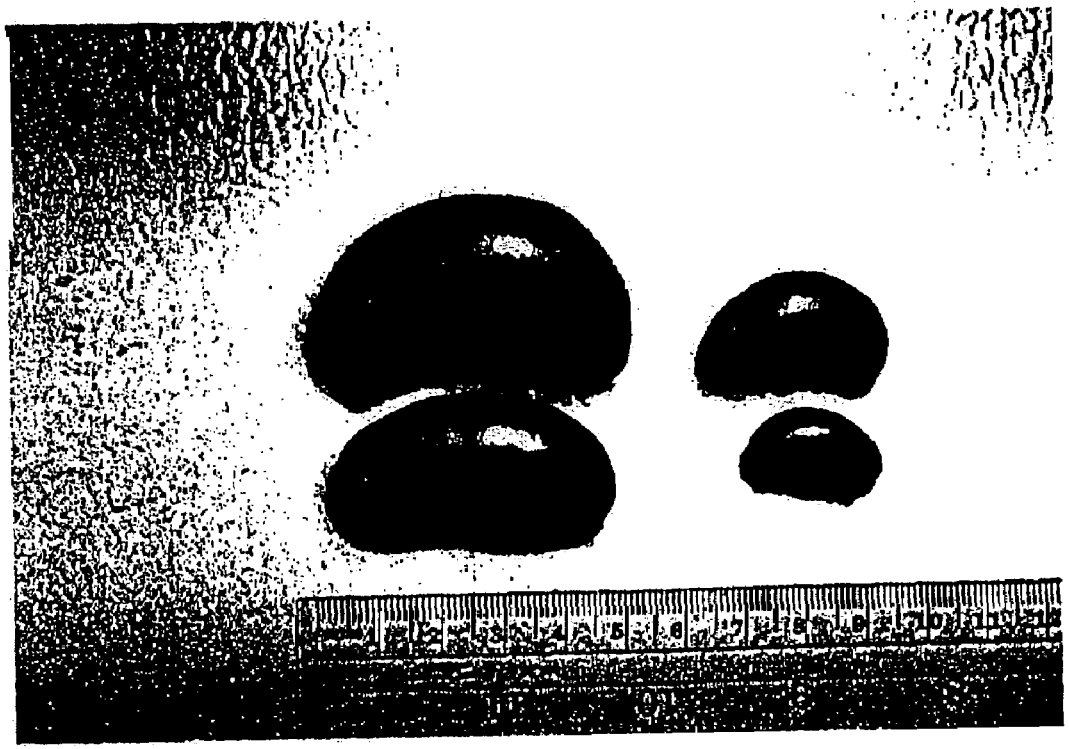
FIG. 19 shows an example of testis from progeny of an immunized turkey and a control turkey.
Figure 20:
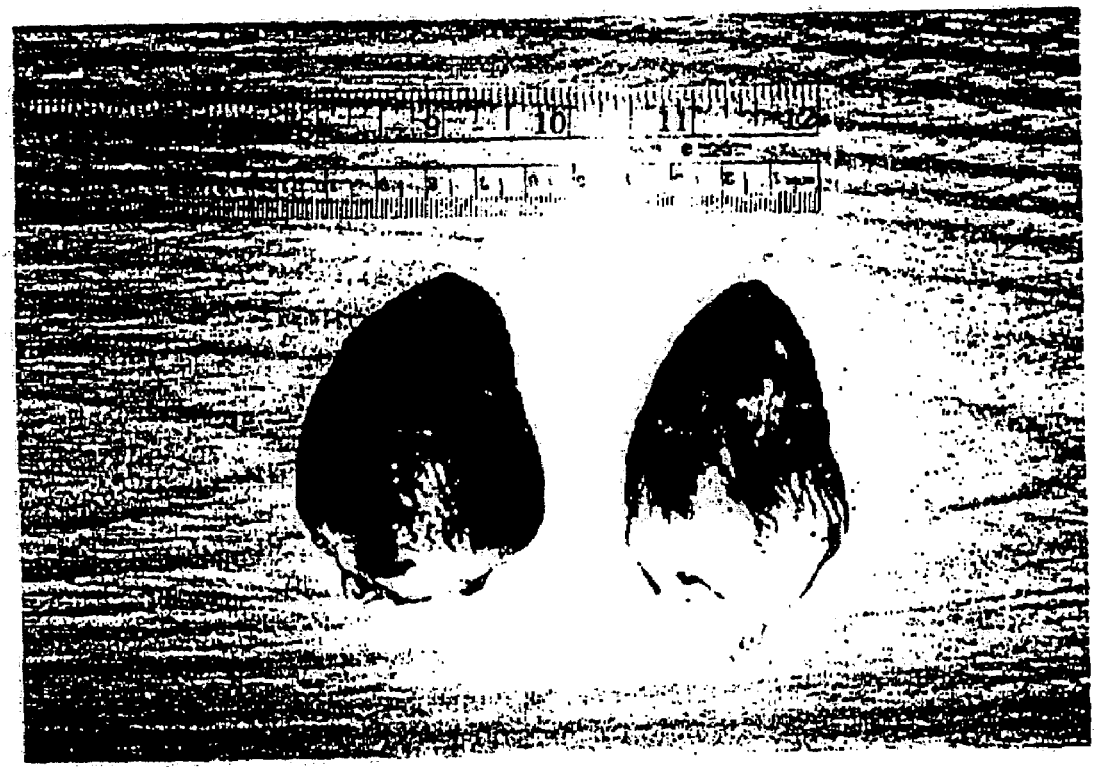
FIG. 20 shows an example of heart muscle from progeny of an immunized turkey and a control turkey.

As used herein, the term "vertebrate" includes but is not limited to non-human vertebrates of the subphylum chordata, including, without limitation, mammals such as cattle, sheep, pigs, goats, and horses; domestic animals such as dogs and cats; and birds, including domestic, wild and game birds such as cocks and hens including chickens, geese, ostrich, turkeys and other gallinaceous birds; and crustaceans, including shrimp and lobster, and fish. Progeny of the vertebrate includes fetuses, eggs, newborns and older progeny.

By "immunogen" is meant a polypeptide or peptide which elicits an immunological response to one or more TGF-beta superfamily polypeptides including a response to myostatin. The term includes molecules that elicit an immunological response without an associated immunological carrier, adjuvant or immunostimulant, and for a myostatin immunogen, a myostatin polypeptide or peptide or a polynucleotide encoding the polypeptide or peptide, capable of being rendered immunogenic, or more immunogenic, by way of association with a carrier molecule, adjuvant or immunostimulant, or by mutation of a wild type myostatin amino acid sequence or a polynucleotide which encodes a wild type myostatin sequence, and/or by incorporation into a molecule containing multiple repeating units of at least one epitope of a myostatin polypeptide. The term may be used to refer to an individual macromolecule or to a homogeneous or heterogeneous population of antigenic macromolecules. For purposes of the present invention, a myostatin immunogen may be derived from any of the various known myostatin sequences, including without limitation, myostatin polypeptides or polynucleotides derived from mouse, rat, human, baboon, cattle, pig, sheep, chicken, turkey, and zebrafish (see, McPherron and Lee, 1997). An immunogen may be homologous to the immunized vertebrate, i.e., turkey myostatin is employed to immunize turkeys, or heterologous thereto, so long as the heterologous immunogen results in the active immunization of the vertebrate and the passive immunization of the progeny of the vertebrate. The immunogen may be recombinantly produced or chemically synthesized.

Additionally, the term "immunogen" includes a polypeptide molecule differing from the reference (wild type) sequence by having one or more amino acid substitutions, deletions and/or additions, i.e., it is a variant polypeptide or peptide, and which has at least about 50% contiguous amino acid identity to the reference molecule, more preferably about 75 to 85% contiguous identity and most preferably about 90 to 95% contiguous identity or more, to the relevant portion of the reference wild type sequence. The amino acid sequence will have no more than about 10-20 amino acid substitutions, or no more than about 5-10 amino acid substitutions, or even only 1, 2, 3 or up to 5 substitutions. Particularly preferred substitutions will generally be conservative in nature, i.e., those substitutions that take place within a family of amino acids. In this regard, amino acids are generally divided into four families: (1) acidic—aspartate and glutamate; (2) basic lysine, arginine, histidine; (3) non-polar alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the activity. In particular, variant polypeptides or peptides which result in the active immunization of a vertebrate to endogenous myostatin, and the passive immunization of its progeny, are within the definition of an immunogen.

A "peptide immunogen" is an immunogen which includes less than the full-length polypeptide molecule and which includes at least one epitope of the polypeptide.

An "epitope" refers to any portion or region of a molecule with the ability or potential to elicit, and combine with, an antibody that binds to a reference polypeptide such as myostatin. For the purpose of the present invention, a polypeptide epitope will usually include at least about 3 amino acids, preferably at least about 5 amino acids, and most preferably at least about 10-15 amino acids to 20-30 or more amino acids, of the reference molecule. There is no critical upper limit to the length of the fragment, which could comprise nearly the full-length of a protein sequence, or even a fusion protein comprising two or more epitopes of a protein in question. Epitopes in polypeptide molecules can be identified using any number of epitope mapping techniques, well known in the art (see Epitope Mapping Protocols, 1996). For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols. Computer programs that formulate hydropathy scales from the amino acid sequence of the protein, utilizing the hydrophobic and hydrophilic properties of each of the 20 amino acids, as described in, e.g., Kyte et al., 1982; and Hopp and Woods, 1981, can also be used to determine antigenic portions of a given molecule. For example, the technique of Hopp and Woods assigns each amino acid a numerical hydrophilicity value and then repetitively averages these values along the peptide chain. The points of highest local average hydrophilicities are indicative of antigenic portions of the molecule.

By "multimer" is meant a molecule having more than one copy of a selected immunogen, e.g., a myostatin peptide or epitope, or multiple tandem repeats of a selected immunogen, e.g., a myostatin peptide or epitope. The myostatin multimer may correspond to a molecule with repeating units of the general formula (MP-X-MP)y wherein MP is a myostatin peptide, X is selected from the group consisting of a peptide linkage, an amino acid spacer group and $[MP]_n$, where n is greater than or equal to 1, y is greater than or equal to 1, and further wherein "MP" may comprise any MP peptide. Y may therefore define 1-40 or more repeating units, more preferably, 1-30 repeating units and most preferably, 1-20 repeating units. Further, the selected myostatin peptide sequences may all be the same, or may correspond to different myostatin sequences so long as they retain the ability to elicit an immune response. Additionally, if the myostatin peptides are linked either chemically or recombinantly to a carrier, myostatin peptides may be linked to either the 5'-end, the 3'-end, or may flank the carrier in question. Further, the myostatin multimer may be located at sites internal to the carrier.

"Homology" refers to the percent identity between two polynucleotide or two polypeptide sequences. Two DNA or polypeptide sequences are "substantially homologous" to each other when the sequences exhibit at least about 75% to 85%, preferably at least about 90%, and most preferably at least about 95% to 98% contiguous sequence identity over a defined length of the sequences.

Percent "identity" between two amino acid or polynucleotide sequences can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN (Dayhoff; Smith and Waterman, 1981), which adapts the local homology algorithm for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, nucleotide sequence relatedness (identity) can be determined by hybridization of polynucleotides under conditions which form stable duplexes between homologous regions. DNA sequences that are substantially homologous can be identified in a Southern hybridization under, for example, stringent conditions, as defined for that particular system (see, e.g., Sambrook et al., 1989). Myostatin polynucleotide sequences useful in the invention hybridize under low, moderate or stringent hybridization conditions to nucleic acid sequences encoding, for example, murine, rat, human, baboon, cattle, pig, sheep, chicken, turkey or zebrafish myostatin (McPherron and Lee, 1997). Low, moderate and stringent hybridization conditions are well known to the art, see, for example, sections 9.47-9.51 of Sambrook et al. (*Molecular Cloning: A Laboratory Manual*, Cold Spring Harbor Laboratory, Cold Spring Harbor, N.Y. (1989). For example, stringent conditions are those that (1) employ low ionic strength and high temperature for washing, for example, 0.015 M NaCl/0.015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Exemplary low stringency conditions include hybridization with a buffer solution of 30 to 25% formamide, 1 M NaCl, 1% SDS (sodium dodecyl sulphate) at 37° C., and a wash in 1× to 2×SSC (20×SSC=3.0 M NaCl/0.3 M trisodium, citrate) at 50 to 55° C. Exemplary moderate stringency conditions include hybridization in 40 to 45% formamide, 1.0 M NaCl, 1% SDS at 37° C., and a wash in 0.5× to 1×SSC at 50 to 60° C. Exemplary high stringency conditions include hybridization in 50% formamide, 1 M NaCl, 1% SDS at 37° C., and a wash in 0.1×SSC at 60 to 65° C.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

An "immunological response" to an immunogen or vaccine is the development in the host of a cellular and/or antibody-mediated immune response to the immunogen of interest. Usually, such a response includes but is not limited to one or more of the following effects; the production of antibodies, B cells, helper T cells, suppressor T cells, and/or cytotoxic T cells and/or γδ T cells, directed specifically to an immunogen or immunogens included in a composition or vaccine of interest. An immunological response can be detected using any of several assays well known in the art, such as standard immunoassays and neutralization assays, including Western blots, dot blots and immunoaffinity assays. The presence of a cell-mediated immunological responses may be determined using CTL cytotoxic cell assays, well known in the art, such as the assay described in Erickson et al., 1993; and Doe et al., 1994.

By immunological "carrier" is meant any molecule which, when associated with an immunogen of interest, imparts immunogenicity to that molecule, or enhances the immunogenicity of the molecule. Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactive virus particles; bacterial toxins such as toxoid from diphtheria, tetanus, cholera, leukotoxin molecules, and the like.

An immunogen is "linked" to a specified carrier molecule when the immunogen is chemically coupled to, or otherwise associated with the carrier, e.g., when the immunogen is expressed from a chimeric DNA molecule which encodes the immunogen and the carrier, i.e., a fusion protein.

An "immunoconjugate" is an immunogen such as a myostatin polypeptide, peptide or multimer which is linked to a carrier by chemical (synthetic) means.

"Adjuvants" refer to agents which act in a nonspecific manner to increase an immune response to a particular antigen, thus reducing the quantity of antigen necessary in any given vaccine, and/or the frequency of injection necessary in order to generate an adequate immune response to the antigen of interest. See, e.g., Allison, 1979.

"Native" or "wild type" proteins, polypeptides or peptides are proteins, polypeptides or peptides isolated from the source in which the proteins naturally occur.

"Recombinant" polypeptides refer to polypeptides produced by recombinant DNA techniques, i.e., produced from cells transformed by an exogenous DNA construct encoding the desired polypeptide. "Synthetic" polypeptides are those prepared by chemical synthesis.

By "polynucleotide" is meant a sequence of nucleotides including, but is not limited to, RNA such as mRNA, cDNA, genomic DNA sequences and even synthetic DNA sequences. The term also includes sequences that include any of the known base analogs of DNA and RNA.

A "vector" is a replicon, such as a plasmid, phage, virus, or cosmid, to which another DNA segment may be attached so as to bring about the replication of the attached segment.

A DNA "coding sequence" or a "sequence encoding" a particular polypeptide, is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

The term DNA "control elements" refers collectively to promoters, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

The term "derived from," as it is used herein, denotes an actual or theoretical source or origin of the subject molecule or immunogen. For example, an immunogen that is "derived from" a particular myostatin molecule will bear close sequence similarity with a relevant portion of the reference molecule. Thus, an immunogen that is "derived from" a particular myostatin molecule may include all of the wild-type myostatin sequence, or may be altered by insertion, deletion or substitution of amino acid residues, so long as the derived sequence provides for an immunogen that corresponds to the targeted myostatin molecule. Immunogens derived from a denoted molecule will contain at least one epitope specific to the denoted molecule.

By "enhancing muscle mass" is meant that the animal administered a vaccine or composition of the invention or its progeny displays an increase in muscle cell size (hypertrophy) and/or muscle cell number (hyperplasia). The increase can be in type 1 and/or type 2 muscle fibers. The term "muscle" as used herein is intended to include analogous tissue types in fish. Methods for determining "enhanced muscle mass" are well known in the art. For example, muscle content can be measured before and after administration of a myostatin immunogen of the invention using standard techniques, such as weighing (Bhasin et al., 1996) and dual-energy x-ray absorptiometry (Bhasin et al., 1999). An increase in muscle size may be evidenced by weight gain of at least about 1% to 10%, preferably 5% to 20%, more preferably at least about 20 to 50% or more, e.g., 100%.

B. Immunogens of the Invention

Immunogens useful in the practice of the invention include members of the TGF-beta superfamily. The use of such an immunogen likely results in antibodies that cross-react with more than one member of the family due to the relatedness of the members of the superfamily. Exemplary immunogens include GDFs, e.g., myostatin (GDF-8), as well as other GDFs (for example, GDF 1-7 and 9-11), inhibins (for example, inhibin-alpha, inhibin-beta-alpha, and inhibin beta-beta), activins, follistatin, macrophage inhibition cytokine (MIC-1), bone morphogenic proteins (BMPs, for example any one of BMP 1-5 or OP-1), Vgr-1, CP-1, MIS, TGF-beta (for example, any one of TGF-beta1, TGF-beta2 or TGF-beta-3) and glial derived neurotrophic factor, the administration of which to a vertebrate likely results in antibodies that recognize at least one and preferably more than one member of the TGF-beta superfamily. Thus, the following description, which relates to myostatin, is exemplary only.

Myostatin is generally composed of a secretory sequence (amino acids 1-262), a proteolytic processing site (amino acids 263-266) and the functional domain at the C-terminus (amino acids 267-375), which has a highly conserved tertiary structure due to the presence of multiple cysteine residues. The nucleotide sequence of the myostatin gene predicts a protein with a molecular weight of approximately 43 kDa. Proteolytic processing releases a 13 kDa peptide containing 9 cysteine residues The invention includes the use of any molecule, e.g., any one of the TGF-beta superfamily, to immunize a vertebrate so as to result in anti-myostatin antibodies. In one embodiment, a myostatin sequence either a polypeptide, peptide or polynucleotide sequence, is employed to immunize a male or female vertebrate. Accordingly, the invention is directed to immunogenic myostatin polypeptides, peptides, multimers, and polynucleotides for use in generating an immune response in a vertebrate which preferably is transmitted to its progeny, i.e., during development. In one embodiment, the method of the invention is employed with egg-laying vertebrates, such as birds and fish. For example, egg-laying birds and fish are immunized to create high antibody titers in maternal serum or plasma. Since antibodies are transferred to the yolk sac of the egg, these antibodies are able to reduce myostatin levels and/or activity during the embryonic period and cause a desired phenotype which is associated with a reduction or decrease in myostatin levels and/or activity. Alternatively, immunization may be intermammalary or in egg-laying vertebrates may be done in ovo. In another embodiment, maternal antibodies are transmitted in utero or in colostrum.

Immunization can be achieved by any of the methods known in the art including, but not limited to, use of polypeptide, peptide or immunoconjugate vaccines or DNA immunization. Such methods are well known to the art, some of which are exemplified below.

I. Myostatin Nucleic Acid Molecules

Sources of nucleotide sequences from which the present nucleic acid molecules encoding myostatin, a fragment (peptide) or a variant thereof, or the nucleic acid complement thereof, include RNA, or genomic DNA or cDNA from any vertebrate, e.g., from cells in physiological fluid or tissue, primary cultures or cell lines. Other sources of the DNA molecules of the invention include genomic or cDNA libraries. Moreover, the present DNA molecules also may be prepared in vitro, e.g., by synthesizing an oligonucleotide of about 30, preferably about 90, more preferably about 150 or more, nucleotides in length, or by subcloning a portion of a DNA segment that encodes a particular myostatin. The myostatin gene from a number of vertebrate species, including mouse, rat, human, baboon, cattle, pig, sheep, chicken, turkey, and zebrafish has been identified and sequenced (McPherron and Lee, 1997), and these sequences can be employed in the practice of the invention or to identify other molecules for use in the invention.

1. Isolation of a Gene Encoding Myostatin

A nucleic acid molecule encoding myostatin of the invention can be identified and isolated using standard methods, as described by Sambrook et al. (1989). For example, reverse-transcriptase PCR (RT-PCR) can be employed to isolate and clone myostatin cDNAs. A primer which is complementary to an RNA encoding myostatin, and preferably hybridizes to the 3' two-thirds of the RNA, can be employed as a primer in a reverse transcriptase reaction to prepare first-strand cDNAs from isolated RNA which contains RNA sequences of interest, e.g., total RNA isolated from an infected avian tissue. RNA can be isolated by methods known to the art, e.g., using TRIZOL reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al. (1987); Erlich (1989). Thus, PCR-based cloning approaches rely upon conserved sequences deduced from alignments of related gene or polypeptide sequences. However, other amplification-based methods known to the art may also be employed, including, but not limited to, self-sustained sequence-specific replication (3SR) (Gebinoga et al.,1996; Fahy et al., 1991; Guatelli et al., 1990), nucleic acid sequence-based amplification (NASBA) (Compton, 1991), strand displacement amplification (SDA) (Walker et al., 1992; Walker et al., 1992), probe cyclization (Landgren et al., 1993), or a Q beta replicase, Sp6, T7, or T3 RNA polymerase based amplification system. See, for example, U.S. Pat. Nos. 5,622,820, 5,629,153, 5,532,126, 5,573,914 and 5,514,545.

Primers are made to correspond to highly conserved regions of peptides or nucleotide sequences which were identified and compared to generate the primers, e.g., by a sequence comparison of myostatin genes. One primer is prepared which is predicted to anneal to the antisense strand, and another primer prepared which is predicted to anneal to the sense strand, of a DNA molecule which encodes myostatin.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, the gel-purified fragment can be directly sequenced.

cDNA or genomic libraries can be screened using the colony hybridization procedure. Generally, each microtiter plate is replicated onto duplicate nitrocellulose filter papers and colonies are allowed to grow at 37° C. for 14-16 hours on L agar containing 50 µg/ml Amp. The colonies are lysed and DNA fixed to the filter by sequential treatment for 5 minutes with 500 mM NaOH, 1.5 M NaCl, and are washed twice for 5 minutes each time with 5× standard saline citrate (SSC). Filters are air dried and baked at 80° C. for 2 hours. The duplicate filters are prehybridized at 42° C. for 6-8 hours with 10 ml per filter of DNA hybridization buffer (5×SSC, pH 7.0, 5 Denhardt's solution (polyvinylpyrrolidine, plus Ficoll and bovine serum albumin; 1×=0.02% of each), 50 mM sodium phosphate buffer at pH 7.0, 0.2% SDS, 20 µg/ml Poly U, and 50 µg/ml denatured salmon sperm DNA).

The samples can be hybridized with kinased probe under conditions which depend on the stringency desired. Typical moderately stringent conditions employ a temperature of 42° C. for 24-36 hours with 1-5 ml/filter of DNA hybridization buffer containing probe. For higher stringencies, high temperatures and shorter times are employed. Generally, the filters are washed four times for 30 minutes each time at 37° C. with 2×SSC, 0.2% SDS and 50 mM sodium phosphate buffer at pH 7, then are washed twice with 2×SSC and 0.2% SDS, air dried, and are autoradiographed at −70° C. for 2 to 3 days.

As used herein, the terms "isolated and/or purified" refer to in vitro isolation of a nucleic acid molecule or peptide molecule from its natural cellular environment, and from association with other components of the cell, such as nucleic acid or polypeptide, so that it can be sequenced, replicated, and/or expressed. For example, "isolated myostatin nucleic acid" is RNA or DNA containing greater than 9, preferably 36, and more preferably 45 or more, sequential nucleotide bases that encode at least a portion of myostatin, or a variant thereof, or a RNA or DNA complementary thereto, that is complementary or hybridizes, respectively, to RNA or DNA encoding the myostatin and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source.

As used herein, the term "recombinant nucleic acid" e.g., recombinant DNA sequence or segment, refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., 1981, and Goeddel et al., 1980. Therefore, DNA includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

2. Variants of the Nucleic Acid Molecules of the Invention

Nucleic acid molecules encoding amino acid sequence variants of myostatin or a nucleic acid sequence variant are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of myostatin.

Oligonucleotide-mediated mutagenesis is a preferred method for preparing amino acid substitution variants of myostatin. This technique is well known in the art as described by Adelman et al. (1983). Briefly, myostatin DNA is altered by hybridizing an oligonucleotide encoding the desired mutation to a DNA template, where the template is the single-stranded form of a plasmid or bacteriophage containing the unaltered or native DNA sequence of myostatin. After hybridization, a DNA polymerase is used to synthesize an entire second complementary strand of the template that will thus incorporate the oligonucleotide primer, and will code for the selected alteration in the myostatin DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. (1987). Thus, the DNA that is to be mutated may be inserted into one of these vectors to generate single-stranded template. Production of the single-stranded template is described in Sections 4.21-4.41 of Sambrook et al. (1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of myostatin, and the other strand (the original template) encodes the native, unaltered sequence of myostatin. This heteroduplex molecule is then transformed into a suitable host cell, usually a prokaryote such as E. coli JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-($\alpha$S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. Coli JM101.

Silent nucleotide substitutions can be ascertained by reference page D1 in Appendix D in Sambrook et al. (1989). Silent nucleotide substitutions can likewise be introduced into DNA segments by methods well known to the art. See, for example, Sambrook et al. (1989). Nucleic acid molecules encoding other myostatins may be modified in a similar manner. Thus, nucleic acid molecules encoding at least a portion of myostatin, or the complement thereto, may be modified so as to yield nucleic acid molecules of the invention having silent nucleotide substitutions, or to yield nucleic acid molecules having nucleotide substitutions that result in amino acid substitutions.

3. Preparation of Myostatin Nucleic Acid Immunogens

Generally, nucleic acid-based vaccines for use with the present invention will include relevant regions encoding a myostatin immunogen, with suitable control sequences and, optionally, ancillary nucleotide sequences. The nucleic acid molecules are preferably prepared in the form of vectors which include the necessary elements to direct transcription and translation of myostatin sequences in a cell.

Once coding sequences for the myostatin immunogens have been prepared or isolated, such sequences can be cloned into any suitable vector or replicon. Numerous cloning vectors are known to those of skill in the art, and the selection of an appropriate cloning vector is a matter of choice. Ligations to other sequences, e.g., ancillary molecules or carrier molecules, are performed using standard procedures, known in the art. One or more myostatin immunogen portions of the chimera can be fused 5' and/or 3' to a desired ancillary sequence or carrier molecule. Alternatively, one or more myostatin immunogen portions may be located at sites internal to the carrier molecule, or such portions can be positioned at both terminal and internal locations in the chimera.

Alternatively, DNA sequences encoding the myostatin immunogens of interest, optionally linked to carrier molecules, can be prepared synthetically rather than cloned. The DNA sequences can be designed with appropriate codons for the particular sequence. The complete sequence of the immunogen is then assembled from overlapping oligonucleotides prepared by standard methods and assembled into a complete coding sequence. See, Edge, 1981, Nambour et al., 1984; Jay et al., 1984.

The coding sequence is then placed under the control of suitable control elements for expression in suitable host tissue in vivo. The choice of control elements will depend on the vertebrate being treated and the type of preparation used. Thus, if the vertebrate's endogenous transcription and translation machinery will be used to express the immunogens, control elements compatible with the particular vertebrate will be utilized.

Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., (1989), as well as a bovine growth hormone terminator sequence. Introns, containing splice donor and acceptor sites, may also be designed into the constructs for use with the present invention.

Enhancer elements may also be used herein to increase expression levels of the constructs. Examples include the SV40 early gene enhancer (Dijkema et al., 1985), the enhancer/promoter derived from the long terminal repeat (LTR) of the Rous Sarcoma Virus (Gorman et al., 1982) and elements derived from human CMV (Boshart et al., 1985), such as elements included in the CMV intron A sequence.

In one embodiment, the myostatin immunogens can also be administered via a carrier virus which expresses the same. Carrier viruses which will find use herein include, but are not limited to, the vaccinia and other pox viruses, adenovirus, retrovirus and herpesvirus. By way of example, vaccinia virus recombinants expressing the proteins can be constructed as follows. The DNA encoding a particular protein is first inserted into an appropriate vector so that it is adjacent to a vaccinia promoter and flanking vaccinia DNA sequences. This vector is then used to transfect cells or immunize a vertebrate to prepare recombinant virus vaccinia.

II. Myostatin Peptides, Immunoconjugates and Multimers

Any myostatin immunogen comprising at least one immunoneutralizing epitope sequence may be employed in the practice of the invention. For example, overlapping peptide sequences based on the myostatin functional domain are synthesized such that the peptides are approximately 10 amino acids in length and overlap adjacent peptide by approximately 5 amino acids. The functional domain of myostatin therefore will result in 22 discrete peptides of 10 amino acids each. A second approach is to identify potential epitopes based upon a three dimensional molecular modeling of myostatin. The presence of 9 cysteine residue will result in a rigid tertiary structure. This can then be compared to the three dimensional structure of other members of the TGF-$\beta$ superfamily such as TGF-$\beta$ who also have multiple cysteine residues. Those regions of myostatin that are exposed or, alternatively that are similar in location to regions of ligands in the TGF-$\beta$ superfamily known to be involved in ligand receptor coupling, would be identified and be evaluated as potential epitopes. The candidate epitope sequences identified may be synthesized on an peptide synthesizer according to generally known procedures. If no cysteine is present in a particular peptide sequence, then a terminal cysteine may be added to the individual sequence to provide a means for conjugation to the carrier.

The myostatin multimer will have more than one copy of selected myostatin immunogens, peptides or epitopes, or multiple tandem repeats of a selected myostatin immunogen, peptide or epitope. Thus, the myostatin multimers may comprise either multiple or tandem repeats of selected myostatin sequences, multiple or tandem repeats of selected myostatin epitopes, or any conceivable combination thereof. Myostatin epitopes may be identified using techniques well known to the art.

For example, the myostatin multimer may correspond to a molecule with repeating units of the general formula (MP-X-MP)y wherein MP is a myostatin peptide, X is selected from the group consisting of a peptide linkage, an amino acid spacer group and $[MP]_n$, where n is greater than or equal to 1, y is greater than or equal to 1, and further wherein "MP' may comprise any MP peptide. Thus, the myostatin multimer may contain from 2-64 or more myostatin peptides, more preferably 2-32 or 2-16 myostatin peptides.

Further, the selected myostatin immunogen sequences may all be the same, or may correspond to different derivatives, analogs, variants or epitopes of myostatin so long as they retain the ability to elicit an immune response. Additionally, if the myostatin immunogens are linked either chemically or recombinantly to a carrier, myostatin peptides may be linked to either the 5'-end, the 3'-end, or may flank the carrier in question. Further, the myostatin multimer may be located at sites internal to the carrier.

Spacer sequences may be present between the myostatin moieties. The strategic placement of various spacer sequences between selected myostatin immunogens can be used to confer increased immunogenicity on the subject constructs. Accordingly, a selected spacer sequence may encode a wide variety of moieties such as a single amino acid linker or a sequence of two to several amino acids. Selected spacer groups may preferably provide enzyme cleavage sites so that the expressed multimer can be processed by proteolytic enzymes in vivo (by APCs, or the like) to yield a number of peptides, each of which contain at least one T-cell epitope derived from the carrier portion, and which are preferably fused to a substantially complete myostatin peptide sequence.

The spacer groups may be constructed so that the junction region between selected myostatin moieties comprises a clearly foreign sequence to the immunized subject, thereby conferring enhanced immunogenicity upon the associated myostatin peptides. Additionally, spacer sequences may be constructed so as to provide T-cell antigenicity, such as those sequences which encode amphipathic and/or a-helical peptide sequences which are generally recognized in the art as providing immunogenic helper T-cell epitopes. The choice of particular T-cell epitopes to be provided by such spacer sequences may vary depending on the particular vertebrate species to be vaccinated.

The myostatin multimeric sequence thus produced renders a highly immunogenic myostatin antigen for use in the compositions of the invention.

In a preferred embodiment, a full length mature myostatin polypeptide is employed to prepare the immunogen. Also preferably, the myostatin polypeptide is closely related in sequence to the endogenous myostatin sequence.

To further increase the immunogenicity of a myostatin polypeptide, peptide or multimer, these molecules are linked to a carrier to form a myostatin immunoconjugate. This is particularly useful if the myostatin immunogen will be administered to the same species from which it is derived.

Suitable carriers are generally polypeptides which include antigenic regions of a protein derived from an infectious material such as a viral surface protein, or a carrier peptide sequence. These carriers serve to non-specifically stimulate T-helper cell activity and to help direct an immunogen of interest to antigen presenting cells (APCs) for processing and presentation at the cell surface in association with molecules of the major histocompatibility complex (MHC).

Several carrier systems have been developed for this purpose. For example, small peptide haptens are often coupled to protein carriers such as keyhole limpet hemocyanin (KLH), bacterial toxins such as tetanus toxoid, diphtheria toxoid ovalbumin, leukotoxin polypeptides, *Pseudomonas* exotoxin and sperm whale myoglobin, to produce an immune response. These coupling reactions typically result in the incorporation of several moles of peptide hapten per mole of carrier protein.

Other suitable carriers for use with the present invention include VP6 polypeptides of rotaviruses, or functional fragments thereof, as disclosed in U.S. Pat. No. 5,071,651. Also useful is a fusion product of a viral protein and one or more epitopes from myostatin, which fusion products are made by the methods disclosed in U.S. Pat. No. 4,722,840. Still other suitable carriers include cells, such as lymphocytes, since presentation in this form mimics the natural mode of presentation in the subject, which gives rise to the immunized state. Alternatively, the myostatin immunogens may be coupled to erythrocytes, preferably the vertebrate's own erythrocytes. Methods of coupling peptides to proteins or cells are known to those of skill in the art.

Preferred carriers include, but are not limited to diphtheria toxoid, tetanus toxoid, KLH, ovalbumin, *Pseudomonas* exotoxin and variants thereof, leukotoxin, fimbrial subunit protein, sperm whale myoglobulin, helper T-cell epitopes such as those disclosed in WO 94/25060, serum albumins, and ovalbumin.

Protein carriers may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl) propionate. Suitable carriers may also be modified to incorporate spacer arms (such as hexamethylene diamine or other bifunctional molecules of similar size) for attachment of peptide immunogens.

Carriers can be physically conjugated to the myostatin immunogen of interest, using standard coupling reactions. Alternatively, chimeric molecules can be prepared recombinantly for use in the present invention, such as by fusing a gene encoding a suitable polypeptide carrier to one or more copies of a gene, or fragment thereof, encoding for a selected myostatin immunogen.

2. Preparation of Peptide-Based Immunogens

The present isolated, purified polypeptides, peptides, and variants thereof, can be synthesized in vitro, e.g., by the solid phase peptide synthetic method or by recombinant DNA approaches. When a myostatin DNA of the invention is expressed in a recombinant cell, it is necessary to purify the recombinant polypeptide from other cell proteins or polypeptides to obtain preparations that are substantially homogenous as to the recombinant myostatin. For example, the culture medium or lysate can be centrifuged to remove particulate cell debris. The membrane and soluble protein fractions are then separated. Myostatin may then be purified from the soluble protein fraction. Alternatively, myostatin may be purified from the insoluble fraction, i.e., refractile bodies (see, for example, U.S. Pat. No. 4,518,526), if necessary.

If expressed as a fusion polypeptide, the fusion polypeptide may be purified by methods specific for the non-myostatin portion of the fusion polypeptide. For example, if the fusion polypeptide is a histidine tagged fusion polypeptide, Ni-NTA resin may be employed to purify the fusion polypeptide.

Myostatin, or a variant thereof, can also be prepared by in vitro transcription and translation reactions. A myostatin expression cassette can be employed to generate myostatin gene-specific transcripts which are subsequently translated in vitro so as to result in a preparation of substantially homogenous myostatin, a variant, or a biologically active fragment thereof. The construction of vectors for use in vitro transcription/translation reactions, as well as the methodologies for such reactions, are well known to the art.

To prepare polypeptide, peptides or variants thereof of the invention, the solid phase peptide synthetic method is preferably employed. The solid phase peptide synthetic method is an established and widely used method, which is described in the following references: Stewart et al., 1969; Merrifield, 1963; Meienhofer, 1973); and Bavaay and Merrifield, 1980). These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography and the like.

Once isolated and characterized, derivatives, e.g., chemically derived derivatives, of a given recombinant myostatin peptide can be readily prepared. For example, amides of the myostatin, or a variant thereof may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or variant of the invention may be prepared in the usual manner by contacting the peptide or variant thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of myostatin or a variant thereof may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide, peptide or variant thereof. Other amino-terminal modifications include aminooxypentane modifications (see Simmons et al., 1997).

In addition, the amino acid sequence of a peptide of the invention can be modified so as to result in a variant. The modification includes the substitution of at least one amino acid residue in the polypeptide or peptide for another amino acid residue, including substitutions which utilize the D rather than L form, as well as other well known amino acid analogs. These analogs include ornithine, homoarginine, phosphoserine, phosphothreonine, phosphotyrosine, hydroxyproline, gamma-carboxyglutarnate; hippuric acid, octahydroindole-2-carboxylic acid, statine, 1,2,3,4,-tetrahydroisoquinoline-3-carboxylic acid, penicillamine, citruline, α-methyl-alanine, para-benzoyl-phenylalanine, phenylglycine, propargylglycine, sarcosine, and tert-butylglycine.

Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

The invention also envisions peptide or polypeptides variants with non-conservative substitutions. Non-conservative substitutions entail exchanging a member of one of the classes described above for another.

Acid addition salts of amino residues of the peptide, polypeptide or variant thereof may be prepared by contacting the peptide or variant with one or more equivalents of the desired inorganic or organic acid, such as, for example, hydrochloric acid. Esters of carboxyl groups of the peptides or variants may also be prepared by any of the usual methods known in the art.

Other modifications include the reduction of cysteinyl thiol groups with 2-mercaptoethanol and carboxymethylated with iodoacetamide as described by Lambden et al. (1981).

Moreover, it is also envisioned that the peptides or polypeptides of the invention are modified in a manner that increases their stability in vivo. These modified agents are termed "derivatives." Methods to prepare such derivatives are well known to the art. One method is to prepare derivatives which are cyclized peptides (see EPA 471,453 (amide bonds); EPA 467,701 (disulfide bonds); EPA 467,699 (thioether bonds)). Other modifications are disclosed in Jameson et al. (*Nature* 368, 744 (1994)); U.S. Pat. No. 4,992,463; and U.S. Pat. No. 5,091,396.

In all of the peptides or polypeptides of the invention, one or more amide linkages (—CO—NH—) may optionally be replaced with another linkage which is an isostere such as —CH$_2$NH—, —CH$_2$S—, —CH$_2$CH$_2$, —CH═CH— (cis and trans), —COCH$_2$—, —CH(OH)CH$_2$— and —CH$_2$SO—. This replacement can be made by methods known in the art. The following references describe preparation of peptide analogs which include these alternative linking moieties: Spatola, 1983a; Spatola, 1983b; Morley, 1980; Hudson et al., 1979 (—CH$_2$NH—), —CH$_2$CH$_2$—); Spatola et al., 1986 (—CH$_2$—S); Hann, 1982 (—CH—CH—, cis and trans); Almquist et al., 1980 (—COCH$_2$—); Jennings-White et al., 1982 (—COCH$_2$—); EP 45665 (1982) (—CH(OH)CH$_2$—); Holladay et al., 1983 (—C(OH)CH$_2$—); and Hruby, 1982 (—CH$_2$—S—).

By "purified and isolated" peptide or polypeptide is meant more than 90% pure, preferably more than 95% pure and more preferably more than 99% pure or is in a completely different context such as that of a pharmaceutical preparation.

Methods for conjugating a peptide to a macromolecule are well known in the art, and are applicable to the preparation of the vaccine of the present invention. Generally, myostatin or a peptide thereof is linked to a carrier protein through a cross linking reagent such as SPDP (N-succinimidyl 3-(2-pyridyldithio)propionate), glutaraldehyde, iminothiolane, N-acetyl-homocysteine thiolactone, bromoalkanoic anhydrides, maleimido-benzoyl-N-hydroxy-succinimide ester, 3-maleimidopropionic acid N-hydroxysuccinimide ester, and the like. Essentially any method where nucleophilic and electrophilic groups are provided on the reacting partners is sufficient to achieve linkage of peptides. The preferred cross linking agent for the present invention providing an electrophilic partner for the coupling reaction are active esters of maleimidoylalkanoic acids, and bromoalkanoic anhydrides. Preferred cross linking partners providing a nucleophile for the coupling reaction are N-acetyl homocysteine thiolactone and imino thiolactone.

Thus, the polypeptides or peptides of the invention may be conjugated or linked to an immunogenic protein, such as KLH or albumin, to enhance their immunogenicity. For example, synthetic peptides are coupled to KLH through the C-terminal cysteine of the peptide using the heterobifunctional reagent N-γ-maleimidobutyric acid N-hydroxysuccinimide ester (GMBS; Sigma). Carrier protein [4 mg KLH ml$^{-1}$ in 100 µl phosphate buffered saline (PBS) pH 7.4] is activated by reaction with GMBS (0.5 mg per 5 µl dimethylformamide) for 1 hour at 25°C under nitrogen gas. The activated protein is separated from excess GMBS by gel filtration on Sephadex G25 (Pharmacia). Column fractions containing the carrier protein (monitored by $A_{280}$) are pooled, and added to 4 mg peptide dissolved in an equivalent volume of PBS. The mixture is gassed with nitrogen, and incubated at 25° C. for 3 hours with gentle stirring. The progress of the conjugation is monitored calorimetrically from reactivity of free cysteine thiol groups with Ellman's reagent. Coupling is complete when no color change is observed. The carrier-conjugated peptides are stored at −20° C. until used.

C. Vaccine and Immunogenic Compositions of the Invention

Once the above molecules are produced, they are formulated into vaccine compositions for delivery to a vertebrate. The relevant myostatin immunogen is administered alone, or mixed with a pharmaceutically acceptable vehicle or excipient. Suitable vehicles are, for example, water, saline, dextrose, glycerol, ethanol, or the like, and combinations thereof. In addition, the vehicle may contain minor amounts of auxiliary substances such as wetting or emulsifying agents, pH buffering agents, or adjuvants which enhance the effectiveness of the vaccine. Suitable adjuvants are described further below. Actual methods of preparing such dosage forms are known, or will be apparent, to those skilled in the art. See, e.g., Remington's Pharmaceutical Sciences, Mack Publishing Company, Easton, Pa., 18th edition, 1990. The composition or formulation to be administered will contain a quantity of the myostatin immunogen adequate to achieve the desired immunized state in the vertebrate being treated.

Thus, preparations comprising a polypeptide, peptide, or nucleic acid molecule of the invention are preferably administered to a vertebrate, e.g., a bird such as a turkey or chicken or a non-human vertebrate, in an amount effective to induce anti-GDF antibodies, e.g., anti-myostatin antibodies, in the vertebrate which can be transmitted or administered to progeny or other vertebrates, such as domestic or farm (livestock), animals. For peptides, polypeptides or nucleic acid molecules of the invention, the dosage required is about 0.01 μg to about 300 mg, preferably about 0.1 μg to about 100 mg, and more preferably about 5 μg to about 50 mg, although other dosages may provide beneficial results. Dosages within these ranges can be administered via bolus doses or via a plurality of unit dosage forms, until the desired effects have been obtained. The amount administered will vary depending on various factors including, but not limited to, the specific immunogen chosen, the weight, physical condition and age of the vertebrate, and the route of inoculation. Thus, the absolute weight of the peptides, polypeptides or nucleic acid molecules included in a given unit dosage form can vary widely, and depends upon factors such as the species, age, weight and physical condition of the vertebrate, as well as the method of administration. Such factors can be readily determined by the veterinarian employing animal models or other test systems which are well known to the art.

Administration of a sense or antisense nucleic acid molecule of the invention may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., 1995; Stevenson et al., 1995; Molling, 1997; Donnelly et al., 1995; Yang et al., 1996; Abdallah et al., 1995). Pharmaceutical formulations, dosages and routes of administration for nucleic acids are generally disclosed, for example, in Felgner et al., supra.

Typically, compositions are prepared for injection or infusion, either as liquid solutions or suspensions. Solid forms suitable for solution in, or suspension in, liquid vehicles prior to injection or infusion may also be prepared. The preparation may also be emulsified. The active ingredient can be mixed with diluents, carriers or excipients which are physiologically acceptable and compatible with the active ingredient(s). Suitable diluents and excipients are, for example, water, saline, PBS, glycerol, or the like, and combinations thereof. In addition, if desired, the compositions may contain minor amounts of auxiliary substances such as wetting or emulsifying agents, stabilizing or pH-buffering agents, and the like.

Such compositions are conventionally administered parenterally, by injection. For example in birds, the composition may be administered intravenously, intramuscularly to breast, lung or thigh, subcutaneously via wing web injection, administration via the beak, spraying the animals or their environment, e.g., their housing or yard, or administration in the drinking water or feed.

Formulations which are suitable for other modes of administration include suppositories, cloaca, insufflated powders or solutions, eye drops, nose drops, intranasal aerosols, and oral formulations.

For other vertebrates, one or more suitable unit dosage forms comprising the agents of the invention, which may optionally be formulated for sustained release (using, for example, liposomes, gels or hydrogels) can be administered by a variety of routes including oral, or parenteral, including by rectal, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

When the agents of the invention are prepared for oral administration, they are preferably combined with a pharmaceutically acceptable diluent or excipient to form a pharmaceutical formulation, or unit dosage form. By "pharmaceutically acceptable" it is meant the diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the agents of the invention can be prepared by procedures known in the art using well known and readily available ingredients. For example, the agent can be formulated with common excipients, or diluents, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

Thus, the agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use. Adjuvants may include for example, emulsifiers, muramyl dipeptides, avridine, aluminum hydroxide, oils, saponins and other substances known in the art. For example, compounds which may serve as emulsifiers herein include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate. Synthetic cationic agents include, for example, cetyltrimethylammonium bromide, while synthetic nonionic agents are exemplified by glyceryl esters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol. Other suitable adjuvants include, but are not limited to, surfactants, e.g., hexadecylamine, octadecylamine, lysolecithin, di-methyldioctadecylammonium bromide, N,N-dioctadecyl-n-N-bis (2-hydroxyethyl-propane di-amine), methoxyhexadecylglycerol, and pluronic polyols; polyanions, e.g., pyran, dextran sulfate, poly IC, polyacrylicacid, carbopol; peptides, e.g., muramyl dipeptide, dimethylglycine, tuftsin, oil emulsions, alum, and mixtures thereof, as well as aluminum compounds such as $Al(OH)_3$, $AlPO_4$, $Al_2(SO_4)_3$, water-in-oil emulsions such as Incomplete Freund's Adjuvant (IFA), Bayol F® or Marcol F®, vitamin-E acetate solubilisate, saponins, muramyl dipeptides in an appropriate solvent such as squalane or squalene, or an adjuvant system comprising squalane, Tween® 80 and Pluronic® L121.

Other suitable adjuvants can be formed with an oil component, such as a single oil, a mixture of oils, a water-in-oil emulsion, or an oil-in-water emulsion. The oil may be a mineral oil, a vegetable oil, or an animal oil. Mineral oil, or oil-in-water emulsions in which the oil component is mineral oil are preferred. In this regard, a "mineral oil" is defined herein as a mixture of liquid hydrocarbons obtained from petrolatum via a distillation technique; the term is synonymous with "liquid paraffin," "liquid petrolatum" and "white mineral oil." The term is also intended to include "light mineral oil," i.e., an oil which is similarly obtained by distillation of petrolatum, but which has a slightly lower specific gravity than white mineral oil. See, e.g., Remington's Pharmaceutical Sciences, supra. A particularly preferred oil component is the oil-in water emulsion sold under the trade name of EMULSIGEN PLUS (comprising a light mineral oil as well as 0.05% formalin, and 30 mcg/mL gentamicin as preservatives), available from MVP Laboratories, Ralston, Nebr., or the VSA-3 adjuvant which is a modified form of the EMULSIGEN PLUS adjuvant. Suitable animal oils include, for example, cod liver oil, halibut oil, menhaden oil, orange roughy oil and shark liver oil, all of which are available commercially. Suitable vegetable oils, include, without limitation, canola oil, almond oil, cottonseed oil, corn oil, olive oil, peanut oil, safflower oil, sesame oil, soybean oil, and the like.

Alternatively, a number of aliphatic nitrogenous bases can be used as adjuvants with the vaccine formulations. For example, known immunologic adjuvants include amines, quaternary ammonium compounds, guanidines, benzamidines and thiouroniums (Gall, 1966). Specific compounds include dimethyldioctadecylammonium bromide (DDA) (available from Kodak) and N,N-dioctadecyl-N,N bis(2-hydroxyethyl)propanediamine ("avridine"). The use of DDA as an immunologic adjuvant has been described. Avridine is also a well-known adjuvant. See, e.g., U.S. Pat. No. 4,310,550, which describes the use of N,N-higher alkyl-N',N1-bis(2 hydroxyethyl)propane diamines in general, and avridine in particular, as vaccine adjuvants. U.S. Pat. No. 5,151,267, and Babink et al., 1986, also relate to the use of avridine as a vaccine adjuvant.

The vaccine compositions of the present invention can also include ancillary substances, such as pharmacological agents, cytokines, or other biological response modifiers. Other ancillary substances include, but are not limited to, substances to increase weight gain, muscle mass or muscle strength, such as growth hormones, growth promoting agents, beta antagonists, partitioning agents and antibiotics.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The vaccines of the present invention are normally prepared as injectables, either as liquid solutions or suspensions, or as solid forms which are suitable for solution or suspension in liquid vehicles prior to injection. The preparation may also be emulsified or the active ingredient encapsulated in liposome vehicles or other particulate carriers used.

The vaccine compositions may also be prepared in solid form. For example, solid particulate formulations can be prepared for delivery from commercially available needleless injector devices. Alternatively, solid dose implants can be provided for implantation into a subject. Controlled, sustained release, delayed release, or any combination thereof, formulations may also be used and are made by incorporating the myostatin immunogens into carriers or vehicles such as liposomes, nonresorbable impermeable polymers such as ethylenevinyl acetate copolymers and HytrelO copolymers, swellable polymers such as hydrogels, or resorbable polymers such as collagen and certain polyacids or polyesters such as those used to make resorbable sutures.

The vertebrate is immunized by administration of one of the above-described vaccine compositions in at least one dose, and preferably two or more doses. Moreover, the animal may be administered as many doses as is required to maintain a state of immunity. The dose/time adjustments associated with the use of vaccines of the present invention can vary considerably and will depend on a variety of factors such as the species of animal to be treated, the particular epitope and/or carrier used, the adjuvant, the age of the animal, and the desired outcome of vaccination. In general, the vaccine is administered by subcutaneous or intramuscular injection into an animal. A single dose of the immunogen of the present invention may be all that is required to achieve immunoneutralization of myostatin, but multiple doses spaced at one to six week intervals, or yearly vaccination for the life of an animal are alternative immunization schemes.

The invention will be further described by the following non-limiting examples.

EXAMPLE 1

To enhance the immunogenicity of myostatin, myostatin was conjugated to a carrier before being introduced into turkey hens. The mature coding region of turkey myostatin DNA (372 base pairs encoding 109 amino acid residues) (FIG. 1) was subcloned into the PQE expression vector system (Qiagen, Inc.) using E. coli strain M15(pREP4) and SG13009 (pREP4). Other fusion protein expression systems may also be employed, e.g., thioredoxin expression vector system (Invitrogen, San Diego) using GI 724 and GI 698 E. coli strains.

Purification His-tag Fusion Proteins. To purify a His-tag fusion protein, a glycerol stock of bacteria is inoculated on LB/ampicillin/kanamycin plates (100 µg/ml ampicilin, 25 µg/ml kanamycin) and incubated overnight at 37° C. A 50 ml liquid culture is inoculated with a single colony and incubated overnight at 37° C. The 50 ml overnight culture is added to 2 L of LB/ampicillin/kanamycin media (100 µg/ml ampicilin, 25 µg/ml kanamycin) at 37° C. Twenty ml of 100 mM IPTG (final concentration 1 mM) is added when a $OD_{600}$=0.5-0.7. The culture is then incubated for 4-6 hours. The cells are collected by centrifugation and resuspended in 20 ml of lysis buffer (8 M urea, 0.1 M $NaH_2PO_4$, 0.01 M Tris-Cl, pH 8.0). Sonication is performed twice. The lysate is centrifuged and the resulting supernatant collected.

One ml of Ni-NTA resin (Qiagen) is mixed with 10 ml of supernatant and incubated for 1 hour. The lysate-resin mixture is loaded onto the column. After the flow through is collected, the column is washed three times with 10 ml of washing buffer (lysis buffer, pH 6.3). The column is eluted twice with 10 ml of elution buffer 1 (lysis buffer, pH 5.9), then twice with 10 ml of elution buffer 2 (lysis buffer, pH 4.5). The eluted sample is subjected to SDS-PAGE. Most of the purified protein is collected in the first elution with elution buffer 2, pH 4.5. The eluted sample is dialyzed against 1× PBS buffer contained 1 M urea, pH 7.0-7.4 and stored at −80° C. N-terminal sequencing of the protein yielded the following sequence: MRGAHHHHHHGSDFGLDXDEHSTESRXXRY (SEQ ID NO:3) FIG. 2 shows a SDS-PAGE analysis with various fusion proteins.

Purification of Thioredoxin Fusion Proteins. A glycerol stock of bacteria with a thio vector redoxin expression is placed on RMG/ampicillin plates (100 µg/ml) and incubated overnight at 30° C. A 50 ml culture is prepared from a single colony by inoculating RM base media/ampicillin (100 µg/ml) and incubating the culture overnight at 30° C. Twenty ml of the overnight culture is added to 2 L of induction media/ampicillin (100 µg/ml with 50 ml of 20% dextrose). Twenty ml of 10 mg/ml L-tryptophan (final concentration 0.1 mg/ml) at pH 5.0 is added at the appropriate OD. The culture is incubated for 4 to 6 hours, then the cells are collected by centrifugation. The cells are resuspended in 20 ml of lysis buffer (8 M urea, 10 mM Tris, 0.1 mM EDTA, pH 8.0), sonicated twice, then subjected to centrifugation. The supernatant is collected and 10 ml of supernatant mixed with 1 ml equilibrated thio-bond resin (Invitrogen). The resin is equilibrated with running buffer (10 mM Tris, 0.1 mM EDTA, 500 mM NaCl, pH 7.0) according to the manufacturer's directions. The mixture is incubated for 1 hour and then loaded onto the column. After flow through is collected, the column is washed three times with 10 ml washing buffer (running buffer with 1 mM 2-mercaptoethanol, ME), then several times with running buffer without ME. The sample is then eluted with running buffer containing 5 mM, 10 mM, 20 mM, 50 mM, 100 mM, 200 mM and 500 mM ME. The majority of the protein is eluted in 50 mM, 100 mM, and 200 mM of ME running buffer. The eluted sample is dialyzed against 1× PBS buffer, pH 7.0-7.4 and stored at −80° C.

Immunization Protocol and Sample Collection. The His-tag myostatin fusion protein was conjugated to KLH and used to immunize $1^{st}$ cycle breeder hens. The turkey hens were injected under the skin on the neck. However, any route or administration means may be employed, e.g., the turkey hens may be injected under the skin under the wing. All sets of turkey hens were subjected to similar if not identical environment conditions such as light and temperature.

The hens were inseminated weekly. The nest was trapped 6 times per day. On day 1 of the vaccination schedule, hens were vaccinated with 125 µg of the immunogen in Freund's complete adjuvant. At thirty-six days post-vaccination hens were light stimulated (15L:9D). Nine and sixteen days later, a blood sample was taken from 20 hens per treatment. A first booster (25 µg in Freund's incomplete adjuvant) was given sixteen days after light stimulation. Ten days later, egg collection began. Subsequent blood samples were drawn at 4, 18, 32, 49, 59, 74, and 88 days after the egg collection began. Subsequent boosts (25 µg) were at 18, 49, and 74 days relative to the egg collection. Titers were determined at 4 and 59 days after the first egg collection.

Results. In the first study, 8 hens were immunized with KLH and 32 with KLH-myostatin. Table 1 shows the anti-myostatin titer in the myostatin-immunized hens versus the control hens (KLH-immunized). The anti-myostatin antibody titer in progeny of these hens was also determined (Table 2). Anti-myostatin antibody levels in myostatin-immunized poults were higher than KLH-immunized poults for at least four weeks after hatching.

In the second study, the body and organ weights for progeny of myostatin- and KLH-immunized birds was determined (Tables 3-7 and FIGS. 3-21). The progeny of myostatin-immunized birds had increased body weight, as well as increased heart, breast muscle and thigh muscle weight, and a decrease in abdominal fat weight. Moreover, as shown in Tables 6 and 7, the increase in body weight was still evident in 6 week old birds from myostatin-immunized hens relative to controls.

TABLE 1

Plasma myostatin antibody titer of turkey hens actively immunized with Keyhole Limpet Hemocyanin (KLH)-myostatin

| Immunization | N | % Myostatin Binding Following Booster Immunization | | |
|---|---|---|---|---|
| | | $1^{st}$ | $2^{nd}$ | $3^{rd}$ |
| KLH | 8 | 0.45 ± 0.06 | 0.47 ± 0.17 | 0.41 ± 0.12 |
| KLH-Myostatin | 32 | 14.89 ± 0.66 | 13.13 ± 0.69 | 15.11 ± 0.67 |

TABLE 2

Maternal myostatin antibody titer (% binding) in poults.

| Treatment | Hen Antibody Titer | Poult Antibody Titer Age | | | | | |
|---|---|---|---|---|---|---|---|
| | | 1 d | 3 d | 1 wk | 2 wk | 3 wk | 4 wk |
| KLH-Immunized | 0.39 ± 0.17 | 0.09 ± 0.01 | 0.04 ± 0.0 | 0.06 ± 0.0 | 0.04 ± 0.01 | 0.04 ± 0.02 | 0.02 ± 0.01 |
| KLH-Myostatin Immunized | 15.9 ± 0.61 | 5.18 ± 0.51 | 4.88 ± 0.54 | 3.32 ± 0.66 | 0.78 ± 0.23 | 0.55 ± 0.12 | 0.40 ± 0.16 |

TABLE 3

| Control | Myostatin Treated |
|---|---|
| Pen 1 (Hens 1-8) | Pen 2 (Hens 9-16) |
| Pen 3 (Hens 17-24) | Pen 4 (Hens 25-32) |
| Pen 5 (Hens 33-40) | Pen 6 (Hens 41-48) |
| Pen 7 (Hens 49-56) | Pen 8 (Hens 57-64) |
| Pen 9 (Hens 65-72) | Pen 10 (Hens 73-80) |
| Pen 11 (Hens 81-88) | Pen 12 (Hens 89-96) |
| Pen 13 (Hens 97-104) | Pen 14 (Hens 105-112) |
| Pen 15 (Hens 113-120) | Pen 16 (Hens 121-128) |

TABLE 4

| Hens/Treatment | Avg. Titer/Hen | Poults Hatched | Avg. Titer/Poult | | |
|---|---|---|---|---|---|
| | | | Hi | Med | Low |
| Control 64 | 0.4507 | 1277 | 0.557 | | |
| Immunized 64 | 13.622 | 1344 | 4.57 | 4.58 | 1.86 |

TABLE 5

Weights of individual muscles and organs from immunized (N = 7) and control (N = 9) male turkeys at 17 weeks of age.

| | Immunized | Control | Immunized vs. Control |
|---|---|---|---|
| Body Weight (Kg) | 15.14 ± −0.35 | 12.5 ± −0.22 | 21% increase with $p < 0.01$ |
| Breast Muscle Weight (Kg) | 3.28 ± −0.13 | 2.45 ± −0.06 | 33% increase with $p < 0.01$ |
| Breast Bone Weight (Kg) | 0.81 ± −0.03 | 0.72 ± −0.03 | No significant change |
| Thigh Muscle Weight (Kg) | 3.50 ± −0.07 | 2.59 ± −0.07 | 35% increase with $p < 0.01$ |
| Abdominal Fat Weight (g) | 47.14 ± −2.9 | 71.1 ± −4.0 | 50% decrease with $p < 0.01$ |
| Testis Weight (g) | 18.35 ± −5.9 | 4.5 ± −1.0 | 300% increase with $p < 0.05$ |
| Gut Weight (g) | 681.5 ± −19.7 | 628.0 ± −21.2 | No significant change |
| Heart Weight (g) | 60.7 ± −3.1 | 48.7 ± −2.9 | 24% increase with $p < 0.05$ |
| Liver Weight (g) | 163.5 ± −6.9 | 156.4 ± −6.4 | No significant change |

TABLE 6

Body weight (gm) of female turkeys maternally immunized with myostatin antibody.

| Treatment | N | Days 1 | Age Weeks | | | | | | | |
|---|---|---|---|---|---|---|---|---|---|---|
| | | | 1 | 2 | 3 | 4 | 5 | 6 | 7 | 9 |
| Control | 21 | 58 ± 1 | 100 ± 8 | 201 ± 16 | 336 ± 23 | 629 ± 23 | 906 ± 47 | 1367 ± 76 | 1766 ± 110 | 3071 ± 179 |
| Immunized | 31 | 57 ± 1 | 100 ± 4 | 214 ± 10 | 363 ± 12 | 637 ± 20 | 962 ± 24 | 1433 ± 46 | 1866 ± 60 | 3305 ± 96 |

TABLE 7

Body weight (gm) of male turkeys maternally immunized with myostatin antibody.

| | | | | | Age | | | | |
|---|---|---|---|---|---|---|---|---|---|
| | | | | | Weeks | | | | |
| Treatment N | Days 1 | 1 | 2 | 3 | 4 | 5 | 6 | 7 | 9 |
| Control 26 | 59 ± 1 | 107 ± 6 | 228 ± 11 | 387 ± 16 | 731 ± 31 | 1017 ± 18 | 1594 ± 66 | 2153 ± 77 | 3733 ± 106 |
| Immunized 37 | 60 ± 1 | 123 ± 4 | 255 ± 8 | 458 ± 17 | 808 ± 28 | 1257 ± 10 | 1725 ± 56 | 2448 ± 75 | 4173 ± 241 |

EXAMPLE 2

Myostatin peptides were prepared. The peptides were C1 (Asn-Met-Leu-Tyr-Phe-Asn-Gly-Lys-Glu-Gln-Ile-Ile-Tyr-Gly-Lys-Ile; residues 5-15; SEQ ID NO:4), D1 (Asp-Cys-Asp-Glu-His-Ser-Thr-Glu-Ser-Arg-Cys; residues 33-41; SEQ ID NO:5), and E1 (Ile-Ala-Pro-Lys-Arg-Tyr-Lys-Ala-Asn; residues 83-98; SEQ ID NO:6). Each received a peptide immunogen and the sequences were chosen based on relative hydrophilicity/hydrophobicity.

The oligopeptides were coupled to the carrier protein KLH using the method of Lerner et al. (1981). Five grams of Sephadex G-25 was equilibrated with 0.05 M sodium phosphate pH=7.0 for about 3 hours at 25° C. The keyhole limpet hemocyanin (KLH, Calbiochem 374805) was dissolved in 0.05 M Na phosphate, pH=6.0 (20 mg/ml). Maleimidobenzoyl-N-hydroxysuccinimide ester (MBS, Calbiochem 442625) was dissolved in N,N-dimethyl formamide (Sigma; 5 mg/100 μl). Two hundred μl of KLH (4 mg) and 10 μl MBS (0.5 mg) was combined and incubated with gentle vortexing for 30 minutes at room temp. The mixture was subjected to centrifugation and the supernatant loaded onto a 10 ml G-25 column. The sample was eluted with 0.05 M Na phosphate pH=7.0, and 12 drop fractions collected. The KLH-MBS elutes around fractions 5-10, and the free KLH and free MBS elute between fractions 10-30. Fractions absorbing at $OD_{280}$ were pooled (about 80% recovery, e.g., 4.5 mg×80%=36 mg). The peptide was solubilized in a minimal amount of water and mixed with KLH-MBS in a 1:1 ratio (5 mg peptide +5 mg KLH-MBS in 4 ml). Na phosphate 0.05 M pH=7.0 was added to a final concentration of 1.25 mg/ml peptide. The mixture was incubated for 3 hours at room temperature with constant shaking. The product is stored at −80°.

Photorefractory Nicholas female turkeys in their second laying cycle were immunized with peptide-KLH preparations (n=4-5 turkey/peptide). Control birds (n=3) were immunized with KLH only. Prior to immunization all turkeys were bled to obtain pre-immune serum. The turkeys were initially injected intradermally with 125 μg of the peptide in Freund's complete adjuvant. Four weeks after the initial immunization, the animals were injected subcutaneously with 25 μg of the peptide prepared with Freund's incomplete adjuvant and then bled within 10-14 days. An injection protocol was performed at monthly intervals (Table 8) for each of the immunized turkeys. Antipeptide antisera were characterized using with recombinant turkey $^{125}$I-GDF (Table 9).

TABLE 8

| Event | Amount | Time Line |
|---|---|---|
| Initial immunization | 125 μg/hen | 0 |
| 1st booster | 25 μg/hen | 4 wks |
| Bleed 1 | — | 6 wks |
| 2nd booster | 25 μg/hen | 8 wks |
| Bleed 2 | — | 10 wks |
| 3rd booster | 25 μg/hen | 12 wks |
| Bleed 3 | — | 14 wks |
| 4th booster | 25 μg/hen | 16 wks |
| Bleed 4 | — | Terminate Experiment |

TABLE 9

Synthetic GDF Titer Levels (% bound)

| Peptide | Hen | Day 0 (1:100) | 6 wks (1:100) | 10 wks (1:100) | Day 0 (1:1000) | 6 wks (1:1000) | 10 wks (1:1000) |
|---|---|---|---|---|---|---|---|
| D1 | 141 | 0.175553 | 0.315367 | 0.589497 | −1.17939 | 0.422191 | 0.428475 |
| | 142 | 0.148847 | 0.410409 | 0.567503 | −1.17939 | 0.781152 | 0.389987 |
| | 143 | −0.01453 | 0.391558 | 0.227394 | −1.17939 | 0.297301 | 0.157487 |
| | 144 | 0.280021 | 0.488956 | 0.162985 | −1.17939 | 0.531372 | 0.290232 |
| | 145 | 0.290232 | 0.475603 | 0.206972 | −1.17939 | 0.230536 | 0.151203 |
| Control | 151 | 1.042714 | 0.35307 | 0.146491 | −1.17939 | 0.254886 | 0.015317 |
| | 152 | 0.413551 | 0.342073 | 0.20383 | −1.17939 | 0.058518 | 0.252529 |
| | 153 | 0.483458 | 0.415907 | 0.354641 | −1.17939 | 0.031812 | 0.03731 |
| C1 | 155 | 0.468534 | 0.029455 | 0.40334 | −1.17939 | 0.283948 | 0.095435 |
| | 156 | 0.421406 | 0.351499 | 0.414336 | −1.17939 | 0.834564 | 0.705747 |
| | 157 | 0.041237 | 0.193619 | 0.167698 | −1.17939 | 0.409624 | 0.023957 |
| | 158 | 0.385274 | 0.231321 | 0.258028 | −1.17939 | 0.569074 | 0.185764 |
| | 159 | 0.432402 | 0.389987 | −0.0538 | −1.17939 | 0.442613 | 0.147276 |

TABLE 9-continued

Synthetic GDF Titer Levels (% bound)

| Peptide | Hen | Day 0 (1:100) | 6 wks (1:100) | 10 wks (1:100) | Day 0 (1:1000) | 6 wks (1:1000) | 10 wks (1:1000) |
|---|---|---|---|---|---|---|---|
| E1 | 160 | 0.476389 | 0.247031 | 0.206972 | −1.17939 | 0.480316 | 0.324007 |
|  | 161 | 0.659404 | 0.13785 | 0.261169 | −1.17939 | 0.321651 | 0.042808 |
|  | 162 | 0.539226 | 0.027099 | 0.355426 | −1.17939 | 0.349928 | 0.27845 |
|  | 163 | 0.415122 | 0.33736 | 0.631127 | −1.17939 | 0.507022 | 0.166127 |
|  | 164 | 0.468534 | 0.367208 | 0.503095 | −1.17939 | 0.192048 | −0.09072 |

REFERENCES

Abdallah et al., *Biol. Cell*, 85:1 1995.
Adelman et al., *DNA*, 2, 183, 1983.
Allison, *J. Reticuloendothel. Soc.*, 26:619-630, 1979.
Almquist et al., *J. Med. Chem.*, 23, 1392-1398, 1980.
Barany et al., The Peptides: Analysis, Synthesis, Biology, editors E. Gross and J. Meinhofer, Vol. 2, Academic Press, New York, (1980), pp. 3-254.
Behringer et al., *Nature*, 345:167, 1990.
Bittle et al., *Nature*, 298:30-33, 1982.
Bhasin et al., *New Eng. J. Med.*, 335:1-7, 1996.
Bhasin et al., *Mol. Endocrinol.*, 13:3155-3162 ,1998.
Bodansky, Principles of Peptide Synthesis, Springer-Verlag, Berlin (1984) Gross and J. Meienhofer, Eds., The Peptides: Analysis, Synthesis, Biology, supra, Vol. 1.
Boshart et al., *Cell*, 41:521, 1985.
Brigham et al., *Am. J. Med. Sci.*, 298:278-281, 1989.
Burke et al., *Nature*, 332:81-82, 1988.
Canonico et al., *Clin. Res.*, 39:219A, 1991.
Casas et al., *J. Anim. Sci.*, 75(Supp 1):149, 1997.
Cheifetz et al., *Cell*, 48:409, 1987.
Clarke et al., *Vaccines*, 88:127-131, 1988.
Compton, *Nature*, 350, 91, 1991.
Crea et al., Proc. Natl. Acad. Sci. U.S.A., 75, 5765, 1978.
Dalbie-McFarland et al., *Proc. Natl. Acad. Sci USA*, 79:6409, 1982.
Davis et al., *Hum. Molec. Genet.*, 2:1847 (1993)Babiuk et al. *Virology*, 159:57-66, 1986.
Dayhoff, M. O. in *Atlas of Protein Sequence and Structure*, M. O. Dayhoff ed., 5 Suppl. 3:353-358, National Biomedical Research Foundation, Washington, D.C.
Delpeyroux et al., *Science*, 233:472-475, 1986.
Dickman, *Science*, 277:1922-1923, 1997.
Dijkema et al., *EMBO LT.*, 4:761, 1985.
Donnelly et al., *Ann. N.Y. Acad. Sci.*, 772, 40, 1995.
Doe et al., *Eur. J. Immunol.*, 24:2369-2376, 1994.
Edge, *Nature*, 292:756, 1981.
Eisenbraun et al., *DNA Cell Biol.*, 12:791, 1993.
Epitope Mapping Protocols in Methods in Molecular Biology, Vol. 66 (Glenn E. Morris, Ed., 1996) Humana Press, Totowa, N.J.
Erlich, ed., *PCR Technology*, (Stockton Press, New York, 1989).
Erickson et al., *J. Immunol.*, 151:4189-4199, 1993.
Fahy et al., *PCR Methods Appl*, 1, 25, 1991.
Fuller et al., *AIDS Res. Human Retrovir.*, 10:1433, 1994.
Fynan et al., *Proc. Natl. Acad. Sci. USA*, 90:12476, 1993.
Gall, D., *Immunology*, 11:369-386, 1966.
Gebinoga et al., *Eur. J. Biochem.*, 235, 256, 1996.
Geisselsoder et al., *BioTechnigues*, 5:786, 1987.
Geysen et al., *Molec. Immunol.*, 23:709-715, 1986.
Geysen et al. *Proc. Natl. Acad. Sci. USA*, 81:3998-4002, 1984.
Goeddel et al., *Nucleic Acids Res.*, 8, 4057, 1980.
Gorman et al., *Proc. Natl. Acad. Sci. USA*, 79:6777, 1982.
Grobet et al., *Natl. Genet.*, 17:71-74, 1997.
Guatelli et al., *Proc. Natl Acad. Sci. U.S.A.*, 87, 1874, 1990.
Hammonds et al., *Molec. Endocrin.*, 5:149, 1991.
Hann, *J. Chem. Soc. Perkins Trans I*, 307-314, 1982.
Haynes et al., *Bio/Technol.*, 4:637-641, 1986.
Hazinski et al., *Am. LT. Respir. Cell Mol. Biol.*, 4:206-209, 1991.
Holladay et al., *Tetrahedron Lett.*, 24, 4401-4404, 1983.
Hruby, *Life Sci.*, 31, 189-199 (1982).
Hopp et al., *Proc. Natl. Acad. Sci. USA*, 78:3824-3828, 1981.
Hudson et al., *Int. J. Pept. Prot. Res.*, 14, 177-185, 1979.
Jennings-White et al., *Tetrahedron Lett.*, 23, 2533 (1982).
Jay et al., *J. Biol. Chem.*, 259:6311, 1984.
Kambadur et al., *Genome Res.*, 7:910-915, 1997.
Kingsman et al., *Vaccines*, 6:304-306, 1988.
Kocamis et al., *Poultry Sci.*, 77, 1913, 1998.
Kunkel, *Proc. Natl. Acad. Sci. USA*, 12:448, 1985.
Kyte et al., *J. Mol. Biol.*, 157:105-132, 1982.
Landgren, *Trends in Gen.*, 9, 199, 1993
Lawn et al., *Nucleic Acids Res.*, 9, 6103, 1981.
Lerner et al., *Proc. Natl. Acad. Sci. USA*, 78, 3403-3407, 1981.
Ling et al., *Nature*, 321:779, 1986.
Lowell et al., *Science* 240:800-802, 1988.
Mason et al., *Biochem, Biophys. Res. Commun.*, 135:957-964, 1986.
Massague, *Cell*, 49:437, 1987.
McPherron et al., *Nature*, 387:83-90, 1997.
McPherron et al., *Proc. Natl. Acad. Sci. U.S.A.*, 94:12457-12461, 1997.
McPherron and Lee, *Proc. Nati. Acad. Sci. USA*, 94:12457-12461, 1997.
Merrifield, *J. Am. Chem. Soc.*, 85 2149, 1963)
Meienhofer in "Hormonal Proteins and Peptides," ed.; C. H. Li, Vol. 2 (Academic Press, 1973), pp. 48-267.
Morein et al., *Nature*, 308:457-460, 1984.
Morley, *Trends Pharm. Sci. pp.* 463-468, 1980.
Molling, *J. Mol. Med.*, 75, 242, 1997.
Mullis et al., *Cold Spring Harbor Symp. Quant. Biol.*, 51, 263, 1987.
Muller et al., *Proc. Natl. Acad. Sci. U.S.A.*, 79:569 573, 1982.
Nabel et al., *Science*, 249:1285-1288, 1990.
Nambair et al., *Science*, 223:1299, 1984.
Padgett et al., *Nature*, 325:81-84, 1987.
Pardoll et al., *Immunity*, 3, 165, 1995.
Raz et al., *Proc. Natl. Acad. Sci. USA*, 91:9519, 1994.

Sambrook et al., *Molecular Cloning: A Laboratory Manual*, Cold Spring Harbor, N.Y. (1989).
Sampath et al., *J. Biol. Chem.*, 265:13198, 1990.
Shahin and Berg, *Can. J. Anim. Sci.*, 65:279 293, 1985.
Shaoquan et al., *Am. J. Physiol.*, 275:R1265-R1273, 1998.
Simmons et al., *Science*, 276, 276, 1997.
Smith and Waterman, *Advances in Appl. Math.*, 2:482-489, 1981.
Spatola, *Vega Data*, 1(3), 1983.
Spatola, in "Chemistry and Biochemistry of Amino Acids Peptides and Proteins," B. Weinstein, eds., Marcel Dekker, New York, p. 267 (1983).
Spatola et al., *Life Sci.*, 38, 1243-1249, 1986.
Stevenson et al., *Immunol. Rev.*, 145, 211, 1995.
Stewart et al., Solid Phase Peptide Synthesis, 2nd Ed., Pierce Chemical Co., Rockford, Ill. (1984).
Tang et al., *Nature*, 358:152, 1992.
The Kodak Laboratory Chemicals Bulletin 56(1):1-5, 1986.
Thomsen et al., *Cell*, 63:485, 1990.
Ulmer et al., *Science*, 258:1745, 1993.
Valenzuela et al., *Bio/Technol.*, 3:323-326, 1985.
Viera et al., *Meth. Enzymol.*, 153, 3, 1987.
Walker et al., *Proc. Natl Acad. Sci. U.S.A.*, 89, 392, 1992.
Walker et al., *Nucl. Acid Res.*, 20, 1691, 1992.
Wang et al., *Proc. Natl. Acad. Sci. USA*, 90:4156, 1993.
Weeks et al., *Cell*, 51:861-867, 1987.
Westhusin, *Nat. Genetics*, 17:4-5, 1997.
Yang et al., *Mol. Med. Today*, 2, 476, 1996.
Zoller et al., *Methods Enzymol.*, 100:468, 1983.

The complete disclosure of all patents, patent documents and publications cited herein are incorporated herein by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

What is claimed is:

1. A method to passively immunize progeny of a female egg laying vertebrate, comprising:
   (a) administering a myostatin immunoconjugate consisting of a mature vertebrate myostatin polypeptide of SEQ ID NO:2 linked to a carrier and optionally linked to a peptide useful for purification or identification, to a female egg laying vertebrate; and
   (b) obtaining progeny from the eggs of the female egg laying vertebrate which comprise anti-myostatin antibodies.

2. The method of claim 1 wherein the vertebrate is a livestock animal.

3. The method of claim 1 wherein the progeny exhibit an increase in body weight, an increase in muscle mass, a reduction in body fat content, an increase in testis size, or any combination thereof.

4. The method of claim 1 wherein the vertebrate is a turkey or chicken.

5. The method of claim 1 wherein the mature vertebrate myostatin polypeptide is an avian myostatin polypeptide.

6. The method of claim 1 wherein the carrier is keyhole limpet hemocyanin.

7. The method of claim 1 wherein the immunoconjugate is a fusion polypeptide.

8. The method of claim 1 wherein the linked peptide is a His-tag.

* * * * *

SEQUENCE LISTING

```
<160> NUMBER OF SEQ ID NOS: 6

<210> SEQ ID NO 1
<211> LENGTH: 333
<212> TYPE: DNA
<213> ORGANISM: Meleagris gallopavo

<400> SEQUENCE: 1
gattttggcc ttgactgcga cgagcactca acggaatctc gatgttgtcg ctacccgctg      60
acagtggatt ttgaagcttt tggatgggac tggattatag cacctaaaag atacaaagcc     120
aattactgct ctggagaatg tgaattcgta tttctacaga aatacccgca cactcacctg     180
gtacaccaag caaatccaag aggctcagca ggcccttgct gcacacccac caagatgtcc     240
cctataaaca tgctgtattt caatggaaaa gaacaaataa tatatggaaa gataccagcc     300
atggttgtag atcgttgcgg gtgctcatga gac                                  333

<210> SEQ ID NO 2
<211> LENGTH: 109
<212> TYPE: PRT
<213> ORGANISM: Meleagris gallopavo

<400> SEQUENCE: 2

Asp Phe Gly Leu Asp Cys Asp Glu His Ser Thr Glu Ser Arg Cys Cys
 1               5                  10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
        50                  55                  60

Asn Pro Arg Gly Ser Ala Gly Pro Cys Cys Thr Pro Thr Leu Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105
```

```
<210> SEQ ID NO 3
<211> LENGTH: 30
<212> TYPE: PRT
<213> ORGANISM: Artificial Sequence
<220> FEATURE:
<223> OTHER INFORMATION: A fusion protein.
<220> FEATURE:
<223> OTHER INFORMATION: Xaa = any amino acid

<400> SEQUENCE: 3

Met Arg Gly Ala His His His His His His Gly Ser Asp Phe Gly Leu
 1               5                  10                  15

Asp Xaa Asp Glu His Ser Thr Glu Ser Arg Xaa Xaa Arg Tyr
            20                  25                  30

<210> SEQ ID NO 4
<211> LENGTH: 16
<212> TYPE: PRT
<213> ORGANISM: Meleagris gallopavo

<400> SEQUENCE: 4

Asn Met Leu Tyr Phe Asn Gly Lys Glu Gln Ile Ile Tyr Gly Lys Ile
 1               5                  10                  15

<210> SEQ ID NO 5
<211> LENGTH: 11
<212> TYPE: PRT
<213> ORGANISM: Meleagris gallopavo

<400> SEQUENCE: 5

Asp Cys Asp Glu His Ser Thr Glu Ser Arg Cys
 1               5                  10

<210> SEQ ID NO 6
<211> LENGTH: 9
<212> TYPE: PRT
<213> ORGANISM: Meleagris gallopavo

<400> SEQUENCE: 6

Ile Ala Pro Lys Arg Tyr Lys Ala Asn
 1               5
```